United States Patent
Ivanov et al.

(10) Patent No.: US 10,739,344 B2
(45) Date of Patent: Aug. 11, 2020

(54) ZINC FINGER LINKER (ZNFL) ANTIBODY

(71) Applicant: West Virginia University, Morgantown, WV (US)

(72) Inventors: Alexey Ivanov, Morgantown, WV (US); Joseph Addison, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 14/979,733

(22) Filed: Dec. 28, 2015

(65) Prior Publication Data
US 2016/0200829 A1 Jul. 14, 2016

Related U.S. Application Data

(60) Provisional application No. 62/097,392, filed on Dec. 29, 2014.

(51) Int. Cl.
*C07K 16/00* (2006.01)
*G01N 33/574* (2006.01)
*C07K 16/18* (2006.01)

(52) U.S. Cl.
CPC ........... *G01N 33/574* (2013.01); *C07K 16/18* (2013.01); *G01N 33/57496* (2013.01); *C07K 2317/34* (2013.01); *G01N 2333/4703* (2013.01)

(58) Field of Classification Search
None
See application file for complete search history.

(56) References Cited

U.S. PATENT DOCUMENTS

2009/0312403 A1* 12/2009 Gaiger ............... A61K 39/0011 514/44 R
2010/0136663 A1* 6/2010 Kim ................... C07K 14/4702 435/252.33

FOREIGN PATENT DOCUMENTS

WO WO2002035981 * 5/2002

OTHER PUBLICATIONS

Addison et al, Cancer Res 75:344-355, online published Nov. 24, 2014.*

* cited by examiner

*Primary Examiner* — Lei Yao
(74) *Attorney, Agent, or Firm* — Buchanan Ingersoll & Rooney PC; Craig G. Cochenour, Esq.

(57) ABSTRACT

The present invention provides a purified antibody that recognizes the conserved zinc fingers linker region (ZnFL) in multiple KRAB-ZNF. The purified antibody recognizes at least one of a conserved zinc finger linker sequence of TGEKPY (SEQ ID NO: 1), TGEKPYK (SEQ ID NO: 2), and TGEKPYE (SEQ ID NO: 3). A method of treating a patient having cancer comprising administering an effective amount of a purified antibody recognizing at least one of a conserved zinc finger linker sequence of TGEKPY (SEQ ID NO: 1), TGEKPYK (SEQ ID NO: 2), and TGEKPYE (SEQ ID NO: 3) is set forth. A diagnostic kit and an affinity matrix detecting one of these conserved zinc finger linker sequences are disclosed. A method of detecting cancerous cells comprising subjecting a cancerous cell to a purified pan-ZNF specific antibody is provided. An antigen is provided that binds to a purified zinc finger linker antibody sequence selected from the group consisting of: SEQ ID NO:1, SEQ ID NO:2, SEQ ID NO:3, SEQ ID NO:4, SEQ ID NO:5, SEQ ID NO:6, SEQ ID NO: 7, SEQ ID NO:8, and SEQ ID NO:9.

11 Claims, 24 Drawing Sheets

Specification includes a Sequence Listing.

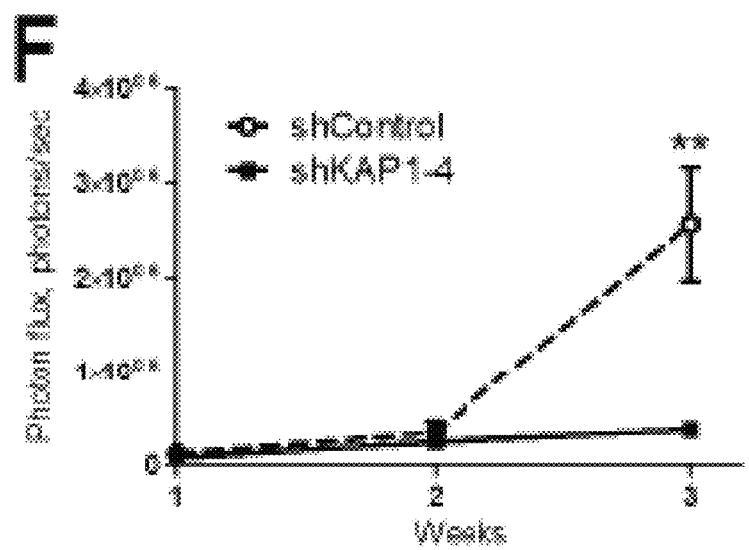
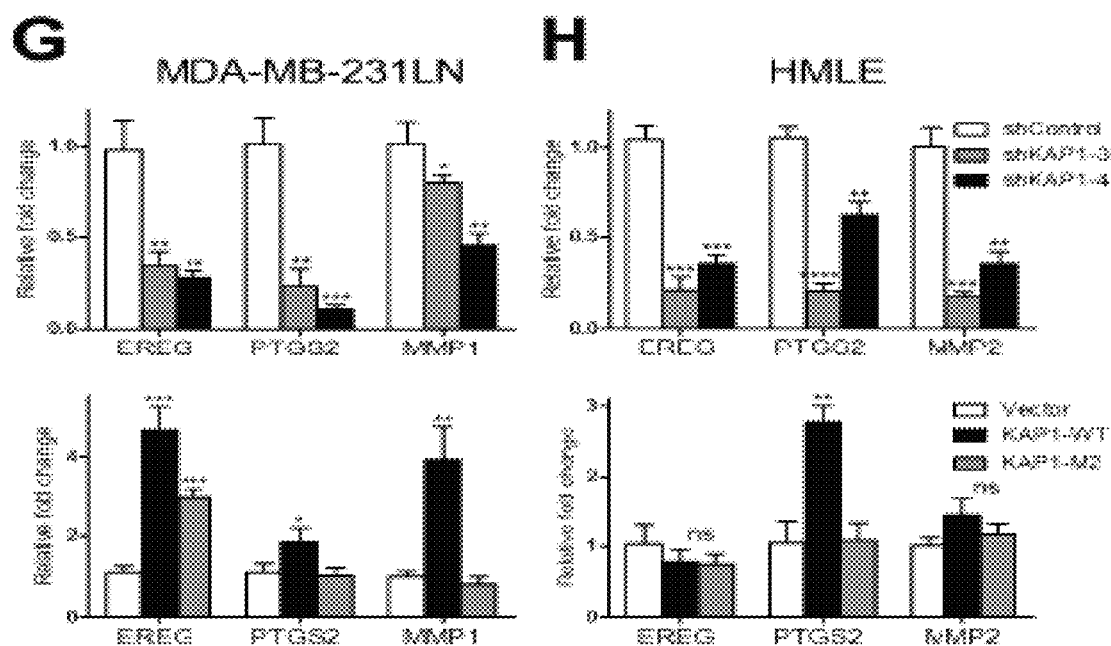
Figure 7 (continued)

ZNF10:

```
                    Linker
ZnF-2-1: -NIHLIQFART TGDKSYK PDNDNSLTH-
ZnF-1-1: -GSSLGISKGIHREKPYE KE GKFFSW-
ZnF1-2:  -RSNLTR QLI TGEKPYE KE GKSFSR-
ZnF2-3:  -SSHLIG QKT TGEEPYE KE GKSFSW-
ZnF3-4:  -FSHLVT QRT TGDKLYT NQ GKSFVH-
ZnF4-5:  -SSRLIR QRT TGEKPYE PE GKSFRQ-
ZnF5-6:  -STHLIL QRT VRVRPYE NE GKSYSQ-
ZnF6-7:  -RSHLVV HRI TGLKPFE KD GKCFSR-
ZnF7-8:  -SSHLYS QRT TGEKPYE HD GKSFSQ-
ZnF8-9:  -SSALIV QRI TGEKPYE CQ GKAFIR-
ZnF9-10: -KNDLIK QRI VGEETYK NQ GIIFSQ-
ZnF10-1: -NSPFIV QIA TGEQFLT NQ GTALVN-
```

ZNF263:

```
                    Linker
ZnF1-2: -NTHLTR QRT TGEKPYQ NI GKCFSC-
ZnF2-3: -NSNLHR QRT TGEKPYK PE GEIFAH-
ZnF3-4: -SSNLLR QRI TGERPYK PE GKSFSR-
ZnF4-5: -SSHLVI ERT ERERLYPFSE GEAVSD-
ZnF5-6: -GMHLTR QRT TGEKPYK TL GENFSH-
ZnF6-7: -RSNLIR QRI TGEKPYT HE GDSFSH-
ZnF7-8: -SSNRIR LRT TGERPYK SE GESFSR-
```

ZNF350:

```
                    Linker
ZnF1-2: -KSWLTD QVM TGEKPHR SL EKAFS-
ZnF2-3: -KFMLTE QRT TGEKPYE PE GKAFL-
ZnF3-4: -KSRLNI QKT TGEKPYI SE GKGFI-
ZnF4-5: -KGNLIV QRI TGEKPYI NE GKGFI-
ZnF5-6: -KTCLIA QRF TGKTPFV SE GKSCS-
ZnF6-7: -KSGLIK QRI TGEKPFE SE GKAFS-
ZnF7-8: -KQKLIV QRT TGERPYG NE GKAFA-
```

Figure 9

| Dataset (# samples) | Fold up TRIM28/KAP1 (tumor vs. normal) | P-value |
|---|---|---|
| <u>Radvanyi Breast (35 vs 9 normal)</u> | | |
| Invasive Ductal BC (32) | 1.648 | 0.016 |
| Ductal BC in Situ (3) | 1.883 | 0.046 |
| <u>Sorlie Breast 2 (93 vs 4 normal)</u> | | |
| Ductal BC (93) | 1.397 | 0.032 |
| <u>Gluck Breast (154 vs 4 normal)</u> | | |
| Invasive BC (154) | 1.270 | 0.014 |
| <u>TCGA Breast array (518 vs 61 normal)</u> | | |
| Mucinous BC (4) | 2.062 | 0.002 |
| Invasive BC (76) | 1.540 | 6.76E-10 |
| Invasive Ductal & Lobular BC (3) | 1.305 | 0.018 |
| Invasive Lobular BC (36) | 1.339 | 1.41E-5 |
| Invasive Ductal BC (392) | 1.439 | 2.50E-9 |
| Mixed Lobular & Ductal BC (7) | 1.247 | 0.024 |

Figure 12 mIP – no SDS (0.5% NP-40, 0.5% Triton X-100)
RIPA – 0.1% SDS
Laemmli – 2% SDS

Schematic representation of KAP1 functional mutants

SEQUENCE LISTING

```
<160> NUMBER OF SEQ ID NOS: 73

<210> SEQ ID NO 1
<211> LENGTH: 6
<212> TYPE: PRT
<213> ORGANISM: artificial sequence
<220> FEATURE:
<223> OTHER INFORMATION: synthetic sequence

<400> SEQUENCE: 1

Thr Gly Glu Lys Pro Tyr
1               5

<210> SEQ ID NO 2
<211> LENGTH: 7
<212> TYPE: PRT
<213> ORGANISM: artificial sequence
<220> FEATURE:
<223> OTHER INFORMATION: synthetic sequence

<400> SEQUENCE: 2

Thr Gly Glu Lys Pro Tyr Lys
1               5
```

```
<210> SEQ ID NO 3
<211> LENGTH: 7
<212> TYPE: PRT
<213> ORGANISM: artificial sequence
<220> FEATURE:
<223> OTHER INFORMATION: synthetic sequence

<400> SEQUENCE: 3

Thr Gly Glu Lys Pro Tyr Glu
1               5

<210> SEQ ID NO 4
<211> LENGTH: 12
<212> TYPE: PRT
<213> ORGANISM: artificial sequence
<220> FEATURE:
<223> OTHER INFORMATION: antibody production sequence

<400> SEQUENCE: 4

His Gln Arg Ile His Thr Gly Glu Lys Pro Tyr Lys
1               5                   10

<210> SEQ ID NO 5
<211> LENGTH: 12
<212> TYPE: PRT
<213> ORGANISM: artificial sequence
<220> FEATURE:
<223> OTHER INFORMATION: antibody production sequence

<400> SEQUENCE: 5

His Gln Arg Ile His Thr Gly Glu Lys Pro Tyr Glu
1               5                   10

<210> SEQ ID NO 6
<211> LENGTH: 12
<212> TYPE: PRT
<213> ORGANISM: artificial sequence
<220> FEATURE:
<223> OTHER INFORMATION: antibody production sequence

<400> SEQUENCE: 6

His Lys Arg Ile His Thr Gly Glu Lys Pro Tyr Lys
1               5                   10

<210> SEQ ID NO 7
<211> LENGTH: 12
<212> TYPE: PRT
<213> ORGANISM: artificial sequence
<220> FEATURE:
<223> OTHER INFORMATION: antibody production sequence

<400> SEQUENCE: 7

His Lys Arg Ile His Thr Gly Glu Lys Pro Tyr Glu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: antibody production sequence

<400> SEQUENCE: 8

His Glu Arg Ile His Thr Gly Glu Lys Pro Tyr Lys
1               5                   10

<210> SEQ ID NO 9
```

-continued

```
<211> LENGTH: 12
<212> TYPE: PRT
<213> ORGANISM: Artificial Sequence
<220> FEATURE:
<223> OTHER INFORMATION: antibody production sequence

<400> SEQUENCE: 9

His Glu Arg Ile His Thr Gly Glu Lys Pro Tyr Glu
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide for immunization and affinity
      purification

<400> SEQUENCE: 10

Cys Gly Gly His Gln Arg Ile His Thr Gly Glu Lys Pro Tyr Lys
1               5                   10                  15

<210> SEQ ID NO 11
<211> LENGTH: 15
<212> TYPE: PRT
<213> ORGANISM: artificial sequence
<220> FEATURE:
<223> OTHER INFORMATION: synthetic peptide for immunization and affinity
      purification

<400> SEQUENCE: 11

Cys Gly Gly His Gln Arg Ile His Thr Gly Glu Lys Pro Tyr Glu
1               5                   10                  15

<210> SEQ ID NO 12
<211> LENGTH: 15
<212> TYPE: PRT
<213> ORGANISM: artificial sequence
<220> FEATURE:
<223> OTHER INFORMATION: synthetic peptide for immunization and affinity
      purification

<400> SEQUENCE: 12

Cys Gly Gly His Lys Arg Ile His Thr Gly Glu Lys Pro Tyr Lys
1               5                   10                  15

<210> SEQ ID NO 13
<211> LENGTH: 15
<212> TYPE: PRT
<213> ORGANISM: artificial sequence
<220> FEATURE:
<223> OTHER INFORMATION: synthetic peptide for immunization and affinity
      purification

<400> SEQUENCE: 13

Cys Gly Gly His Lys Arg Ile His Thr Gly Glu Lys Pro Tyr Glu
1               5                   10                  15

<210> SEQ ID NO 14
<211> LENGTH: 15
<212> TYPE: PRT
<213> ORGANISM: artificial sequence
<220> FEATURE:
<223> OTHER INFORMATION: synthetic peptide for immunization and affinity
      purification

<400> SEQUENCE: 14

Cys Gly Gly His Glu Arg Ile His Thr Gly Glu Lys Pro Tyr Lys
```

```
<210> SEQ ID NO 15
<211> LENGTH: 15
<212> TYPE: PRT
<213> ORGANISM: artificial sequence
<220> FEATURE:
<223> OTHER INFORMATION: synthetic peptide for immunization and affinity
      purification

<400> SEQUENCE: 15

Cys Gly Gly His Glu Arg Ile His Thr Gly Glu Lys Pro Tyr Glu
1               5                   10                  15

<210> SEQ ID NO 16
<211> LENGTH: 14
<212> TYPE: PRT
<213> ORGANISM: artificial sequence
<220> FEATURE:
<223> OTHER INFORMATION: synthetic peptide for immunization and affinity
      purification

<400> SEQUENCE: 16

Gly His Gln Arg Ile His Thr Gly Glu Lys Pro Tyr Lys Cys
1               5                   10

<210> SEQ ID NO 17
<211> LENGTH: 14
<212> TYPE: PRT
<213> ORGANISM: artificial sequence
<220> FEATURE:
<223> OTHER INFORMATION: synthetic peptide for immunization and affinity
      purification

<400> SEQUENCE: 17

Gly His Gln Arg Ile His Thr Gly Glu Lys Pro Tyr Glu Cys
1               5                   10

<210> SEQ ID NO 18
<211> LENGTH: 14
<212> TYPE: PRT
<213> ORGANISM: artificial sequence
<220> FEATURE:
<223> OTHER INFORMATION: synthetic peptide for immunization and affinity
      purification

<400> SEQUENCE: 18

Gly His Lys Arg Ile His Thr Gly Glu Lys Pro Tyr Lys Cys
1               5                   10

<210> SEQ ID NO 19
<211> LENGTH: 14
<212> TYPE: PRT
<213> ORGANISM: artificial sequence
<220> FEATURE:
<223> OTHER INFORMATION: synthetic peptide for immunization and affinity
      purification

<400> SEQUENCE: 19

Gly His Lys Arg Ile His Thr Gly Glu Lys Pro Tyr Glu Cys
1               5                   10

<210> SEQ ID NO 20
<211> LENGTH: 14
<212> TYPE: PRT
<213> ORGANISM: artificial sequence
<220> FEATURE:
<223> OTHER INFORMATION: synthetic peptide for immunization and affinity
``` purification

<400> SEQUENCE: 20

Gly His Glu Arg Ile His Thr Gly Glu Lys Pro Tyr Lys Cys
1               5                   10

<210> SEQ ID NO 21
<211> LENGTH: 14
<212> TYPE: PRT
<213> ORGANISM: artificial sequence
<220> FEATURE:
<223> OTHER INFORMATION: synthetic peptide for immunization and affinity
      purification

<400> SEQUENCE: 21

Gly His Glu Arg Ile His Thr Gly Glu Lys Pro Tyr Glu Cys
1               5                   10

<210> SEQ ID NO 22
<211> LENGTH: 21
<212> TYPE: DNA
<213> ORGANISM: Homo sapiens

<400> SEQUENCE: 22
ttcaagcaat tcaacaagtt a                                              21

<210> SEQ ID NO 23
<211> LENGTH: 21
<212> TYPE: DNA
<213> ORGANISM: Homo sapiens

<400> SEQUENCE: 23
ccgcatgttc aagcaattca a                                              21

<210> SEQ ID NO 24
<211> LENGTH: 21
<212> TYPE: DNA
<213> ORGANISM: Homo sapiens

<400> SEQUENCE: 24
tacaacctta ttgttattga a                                              21

<210> SEQ ID NO 25
<211> LENGTH: 20
<212> TYPE: DNA
<213> ORGANISM: Homo sapiens

<400> SEQUENCE: 25
tctcgcttgg gcgagagtaa                                                20

<210> SEQ ID NO 26
<211> LENGTH: 19
<212> TYPE: DNA
<213> ORGANISM: Homo sapiens

<400> SEQUENCE: 26
gccccaagag tcacaagag                                                 19

<210> SEQ ID NO 27
<211> LENGTH: 22
<212> TYPE: DNA
<213> ORGANISM: Homo sapiens

<400> SEQUENCE: 27
cacagccatg tcttcaatct tc                                            22

<210> SEQ ID NO 28
<211> LENGTH: 19
<212> TYPE: DNA
<213> ORGANISM: Homo sapiens

<400> SEQUENCE: 28
acaggcttcc attgaccag                                                19

<210> SEQ ID NO 29
<211> LENGTH: 21
<212> TYPE: DNA
<213> ORGANISM: Homo sapiens

<400> SEQUENCE: 29
tcaccataga gtgcttccaa c                                             21

<210> SEQ ID NO 30
<211> LENGTH: 21
<212> TYPE: DNA
<213> ORGANISM: Homo sapiens

<400> SEQUENCE: 30
gaatatgtgg ctttgaccgt g                                             21

<210> SEQ ID NO 31
<211> LENGTH: 20
<212> TYPE: DNA
<213> ORGANISM: Homo sapiens

<400> SEQUENCE: 31
tggatcccct gaggtaactc                                               20

<210> SEQ ID NO 32
<211> LENGTH: 23
<212> TYPE: DNA
<213> ORGANISM: Homo sapiens

<400> SEQUENCE: 32
aaggaccata ctgtgcgctc tac                                           23

<210> SEQ ID NO 33
<211> LENGTH: 25
<212> TYPE: DNA
<213> ORGANISM: Homo sapiens

<400> SEQUENCE: 33
acgttgcaat agacagtacg ttcac                                         25

<210> SEQ ID NO 34
<211> LENGTH: 18
<212> TYPE: DNA
<213> ORGANISM: Homo sapiens

<400> SEQUENCE: 34
tgtttgacgg catcccac                                                 18

<210> SEQ ID NO 35
<211> LENGTH: 20
<212> TYPE: DNA
<213> ORGANISM: Homo sapiens

<400> SEQUENCE: 35
ctgtcactgc ctggtacttc                                               20

<210> SEQ ID NO 36
<211> LENGTH: 20
<212> TYPE: DNA
<213> ORGANISM: Homo sapiens

<400> SEQUENCE: 36
gatttgggtc gcagttcttg                                               20

<210> SEQ ID NO 37
<211> LENGTH: 23
<212> TYPE: DNA
<213> ORGANISM: Homo sapiens

<400> SEQUENCE: 37
ccttatcttg gatctttgcc ttg                                           23

<210> SEQ ID NO 38
<211> LENGTH: 19
<212> TYPE: DNA
<213> ORGANISM: Homo sapiens

<400> SEQUENCE: 38
gtctctttgg tgcagctca                                                19

<210> SEQ ID NO 39
<211> LENGTH: 22
<212> TYPE: DNA
<213> ORGANISM: Homo sapiens

<400> SEQUENCE: 39
atcttcggcc cttagtgtaa tg                                            22

<210> SEQ ID NO 40
<211> LENGTH: 21
<212> TYPE: DNA
<213> ORGANISM: Homo sapiens

<400> SEQUENCE: 40
ttgtagactt ggaacccaca g                                             21

<210> SEQ ID NO 41
<211> LENGTH: 21
<212> TYPE: DNA
<213> ORGANISM: Homo sapiens

<400> SEQUENCE: 41
atctccttgc caatggtgta g                                             21

<210> SEQ ID NO 42
<211> LENGTH: 21
<212> TYPE: DNA
<213> ORGANISM: Homo sapiens

<400> SEQUENCE: 42
actgaaggtg tagctagggt a                                             21

<210> SEQ ID NO 43
<211> LENGTH: 22
<212> TYPE: DNA
<213> ORGANISM: Homo sapiens

<400> SEQUENCE: 43
tgaagatgaa aggtggacca ac          22

<210> SEQ ID NO 44
<211> LENGTH: 26
<212> TYPE: DNA
<213> ORGANISM: homo sapiens

<400> SEQUENCE: 44
agaatgggag agtccaagag aatggc          26

<210> SEQ ID NO 45
<211> LENGTH: 21
<212> TYPE: DNA
<213> ORGANISM: Homo sapiens

<400> SEQUENCE: 45
ccaaggtcaa tgtcaggaga g          21

<210> SEQ ID NO 46
<211> LENGTH: 20
<212> TYPE: DNA
<213> ORGANISM: Homo sapiens

<400> SEQUENCE: 46
gcacccattt acacctacac          20

<210> SEQ ID NO 47
<211> LENGTH: 25
<212> TYPE: DNA
<213> ORGANISM: Homo sapiens

<400> SEQUENCE: 47
atgacatcaa gggcattcag gagct          25

<210> SEQ ID NO 48
<211> LENGTH: 28
<212> TYPE: PRT
<213> ORGANISM: Homo sapiens

<400> SEQUENCE: 48

Asn Ile His Leu Ile Gln Phe Ala Arg Thr His Thr Gly Asp Lys Ser
1               5                   10                  15

Tyr Lys Cys Pro Asp Asn Asp Asn Ser Leu Thr His
            20                  25

<210> SEQ ID NO 49
<211> LENGTH: 27
<212> TYPE: PRT
<213> ORGANISM: Homo sapiens

<400> SEQUENCE: 49

Gly Ser Ser Leu Gly Ile Ser Lys Gly Ile His Arg Glu Lys Pro Tyr
1               5                   10                  15

Glu Cys Lys Glu Cys Gly Lys Phe Phe Ser Trp
            20                  25

<210> SEQ ID NO 50
<211> LENGTH: 28
<212> TYPE: PRT
<213> ORGANISM: Homo sapiens

<400> SEQUENCE: 50

Arg Ser Asn Leu Thr Arg His Gln Leu Ile His Thr Gly Glu Lys Pro
1               5                   10                  15

Tyr Glu Cys Lys Glu Cys Gly Lys Ser Phe Ser Arg
                20                  25

<210> SEQ ID NO 51
<211> LENGTH: 29
<212> TYPE: PRT
<213> ORGANISM: Homo sapiens

<400> SEQUENCE: 51

Ser Ser His Leu Leu Ile Gly His Gln Lys Thr His Thr Gly Glu Glu
1               5                   10                  15

Pro Tyr Glu Cys Lys Glu Cys Gly Lys Ser Phe Ser Trp
                20                  25

<210> SEQ ID NO 52
<211> LENGTH: 28
<212> TYPE: PRT
<213> ORGANISM: Homo sapiens

<400> SEQUENCE: 52

Phe Ser His Leu Val Thr His Gln Arg Thr His Thr Gly Asp Lys Leu
1               5                   10                  15

Tyr Thr Cys Asn Gln Cys Gly Lys Ser Phe Val His
                20                  25

<210> SEQ ID NO 53
<211> LENGTH: 28
<212> TYPE: PRT
<213> ORGANISM: Homo sapiens

<400> SEQUENCE: 53

Ser Ser Arg Leu Ile Arg His Gln Arg Thr His Thr Gly Glu Lys Pro
1               5                   10                  15

Tyr Glu Cys Pro Glu Cys Gly Lys Ser Phe Arg Gln
                20                  25

<210> SEQ ID NO 54
<211> LENGTH: 28
<212> TYPE: PRT
<213> ORGANISM: Homo sapiens

<400> SEQUENCE: 54

Ser Thr His Leu Ile Leu His Gln Arg Thr His Val Arg Val Arg Pro
1               5                   10                  15

Tyr Glu Cys Asn Glu Cys Gly Lys Ser Tyr Ser Gln
                20                  25

<210> SEQ ID NO 55
<211> LENGTH: 28
<212> TYPE: PRT
<213> ORGANISM: Homo sapiens

<400> SEQUENCE: 55

Arg Ser His Leu Val Val His Arg Ile His Thr Gly Leu Lys Pro
1               5                   10                  15

Phe Glu Cys Lys Asp Cys Gly Lys Cys Phe Ser Arg
                20                  25

<210> SEQ ID NO 56

-continued

<211> LENGTH: 28
<212> TYPE: PRT
<213> ORGANISM: Homo sapiens

<400> SEQUENCE: 56

Ser Ser His Leu Tyr Ser His Gln Arg Thr His Thr Gly Glu Lys Pro
1               5                   10                  15

Tyr Glu Cys His Asp Cys Gly Lys Ser Phe Ser Gln
            20                  25

<210> SEQ ID NO 57
<211> LENGTH: 28
<212> TYPE: PRT
<213> ORGANISM: Homo sapiens

<400> SEQUENCE: 57

Ser Ser Ala Leu Ile Val His Gln Arg Ile His Thr Gly Glu Lys Pro
1               5                   10                  15

Tyr Glu Cys Cys Gln Cys Gly Lys Ala Phe Ile Arg
            20                  25

<210> SEQ ID NO 58
<211> LENGTH: 28
<212> TYPE: PRT
<213> ORGANISM: Homo sapiens

<400> SEQUENCE: 58

Lys Asn Asp Leu Ile Lys His Gln Arg Ile His Val Gly Glu Glu Thr
1               5                   10                  15

Tyr Lys Cys Asn Gln Cys Gly Ile Ile Phe Ser Gln
            20                  25

<210> SEQ ID NO 59
<211> LENGTH: 28
<212> TYPE: PRT
<213> ORGANISM: Homo sapiens

<400> SEQUENCE: 59

Asn Ser Pro Phe Ile Val His Gln Ile Ala His Thr Gly Glu Gln Phe
1               5                   10                  15

Leu Thr Cys Asn Gln Cys Gly Thr Ala Leu Val Asn
            20                  25

<210> SEQ ID NO 60
<211> LENGTH: 27
<212> TYPE: PRT
<213> ORGANISM: Homo sapiens

<400> SEQUENCE: 60

Asn Thr His Leu Thr Arg His Arg Thr His Thr Gly Glu Lys Pro Tyr
1               5                   10                  15

Gln Cys Asn Ile Cys Gly Lys Cys Phe Ser Cys
            20                  25

<210> SEQ ID NO 61
<211> LENGTH: 28
<212> TYPE: PRT
<213> ORGANISM: Homo sapiens

<400> SEQUENCE: 61

Asn Ser Asn Leu His Arg His Gln Arg Thr His Thr Gly Glu Lys Pro
1               5                   10                  15

```
Tyr Lys Cys Pro Glu Cys Gly Glu Ile Phe Ala His
            20                  25
```

<210> SEQ ID NO 62
<211> LENGTH: 28
<212> TYPE: PRT
<213> ORGANISM: Homo sapiens

<400> SEQUENCE: 62

```
Ser Ser Asn Leu Leu Arg His Gln Arg Ile His Thr Gly Glu Arg Pro
1               5                   10                  15

Tyr Lys Cys Pro Glu Cys Gly Lys Ser Phe Ser Arg
            20                  25
```

<210> SEQ ID NO 63
<211> LENGTH: 28
<212> TYPE: PRT
<213> ORGANISM: Homo sapiens

<400> SEQUENCE: 63

```
Ser Ser His Leu Val Ile His Glu Arg Thr His Glu Arg Glu Arg Leu
1               5                   10                  15

Tyr Pro Phe Ser Glu Cys Gly Glu Ala Val Ser Asp
            20                  25
```

<210> SEQ ID NO 64
<211> LENGTH: 28
<212> TYPE: PRT
<213> ORGANISM: Homo sapiens

<400> SEQUENCE: 64

```
Gly Met His Leu Thr Arg His Gln Arg Thr His Thr Gly Glu Lys Pro
1               5                   10                  15

Tyr Lys Cys Thr Leu Cys Gly Glu Asn Phe Ser His
            20                  25
```

<210> SEQ ID NO 65
<211> LENGTH: 28
<212> TYPE: PRT
<213> ORGANISM: Homo sapiens

<400> SEQUENCE: 65

```
Arg Ser Asn Leu Ile Arg His Gln Arg Ile His Thr Gly Glu Lys Pro
1               5                   10                  15

Tyr Thr Cys His Glu Cys Gly Asp Ser Phe Ser His
            20                  25
```

<210> SEQ ID NO 66
<211> LENGTH: 28
<212> TYPE: PRT
<213> ORGANISM: Homo sapiens

<400> SEQUENCE: 66

```
Ser Ser Asn Arg Ile Arg His Leu Arg Thr His Thr Gly Glu Arg Pro
1               5                   10                  15

Tyr Lys Cys Ser Glu Cys Gly Glu Ser Phe Ser Arg
            20                  25
```

<210> SEQ ID NO 67
<211> LENGTH: 27
<212> TYPE: PRT
<213> ORGANISM: Homo sapiens

<400> SEQUENCE: 67

Lys Ser Trp Leu Thr Asp His Gln Val Met His Thr Gly Glu Lys Pro
1               5                   10                  15

His Arg Cys Ser Leu Cys Glu Lys Ala Phe Ser
            20                  25

<210> SEQ ID NO 68
<211> LENGTH: 27
<212> TYPE: PRT
<213> ORGANISM: Homo sapiens

<400> SEQUENCE: 68

Lys Phe Met Leu Thr Glu His Gln Arg Thr His Thr Gly Glu Lys Pro
1               5                   10                  15

Tyr Glu Cys Pro Glu Cys Gly Lys Ala Phe Leu
            20                  25

<210> SEQ ID NO 69
<211> LENGTH: 27
<212> TYPE: PRT
<213> ORGANISM: Homo sapiens

<400> SEQUENCE: 69

Lys Ser Arg Leu Asn Ile His Gln Lys Thr His Thr Gly Glu Lys Pro
1               5                   10                  15

Tyr Ile Cys Ser Glu Cys Gly Lys Gly Phe Ile
            20                  25

<210> SEQ ID NO 70
<211> LENGTH: 27
<212> TYPE: PRT
<213> ORGANISM: Homo sapiens

<400> SEQUENCE: 70

Lys Gly Asn Leu Ile Val His Gln Arg Ile His Thr Gly Glu Lys Pro
1               5                   10                  15

Tyr Ile Cys Asn Glu Cys Gly Lys Gly Phe Ile
            20                  25

<210> SEQ ID NO 71
<211> LENGTH: 27
<212> TYPE: PRT
<213> ORGANISM: Homo sapiens

<400> SEQUENCE: 71

Lys Thr Cys Leu Ile Ala His Gln Arg Phe His Thr Gly Lys Thr Pro
1               5                   10                  15

Phe Val Cys Ser Glu Cys Gly Lys Ser Cys Ser
            20                  25

<210> SEQ ID NO 72
<211> LENGTH: 27
<212> TYPE: PRT
<213> ORGANISM: Homo sapiens

<400> SEQUENCE: 72

Lys Ser Gly Leu Ile Lys His Gln Arg Ile His Thr Gly Glu Lys Pro
1               5                   10                  15

Phe Glu Cys Ser Glu Cys Gly Lys Ala Phe Ser
            20                  25

```
<210> SEQ ID NO 73
<211> LENGTH: 27
<212> TYPE: PRT
<213> ORGANISM: Homo sapiens

<400> SEQUENCE: 73

Lys Gln Lys Leu Ile Val His Gln Arg Thr His Thr Gly Glu Arg Pro
1               5                   10                  15

Tyr Gly Cys Asn Glu Cys Gly Lys Ala Phe Ala
            20                  25
```

ZINC FINGER LINKER (ZNFL) ANTIBODY

CROSS-REFERENCE TO RELATED APPLICATION

This utility non-provisional patent application claims the benefit of priority to U.S. Provisional Patent Application Ser. No. 62/097,392, filed Dec. 29, 2014. The entire contents of U.S. Provisional Patent Application Ser. No. 62/097,392 is incorporated by reference into this utility non-provisional patent application as if fully rewritten herein.

STATEMENT REGARDING FEDERALLY SPONSORED RESEARCH OR DEVELOPMENT

This invention was made with government support under Grant Nos. R01CA148671 and P30CA125123 awarded by the National Institute of Health/National Cancer Institute, and in part by Grant No. 5P20RR016440 awarded by the National Institute of Health/NCRR and Grant No. 5P20GM103434 awarded by National Institute of Health/WV-INBRE. The government has certain rights in the invention.

SEQUENCE LISTING

Following the Abstract of The Disclosure is set forth a paper copy of the SEQUENCE LISTING in written form (.PDF format) having SEQ ID NO:1 through SEQ ID NO:73. The paper copy of the SEQUENCE LISTING is incorporated by reference into this application. A SEQUENCE LISTING in computer-readable form (.txt file) also accompanies this application with a Statement of Identity Of Computer-Readable Form And Written Sequence Listing.

BACKGROUND OF THE INVENTION

1. Field of the Invention

This invention provides a purified zinc finger linker (ZnFL) antibody. This invention shows that KAP1 promotes proliferation and metastatic progression of breast cancer cells, and that KAP1 stabilizes KRAB-ZNFs and promotes mammary tumorigenesis. This invention elucidates the role of an important developmental transcription network in promoting breast cancer growth and metastasis, and provides a method for a broad-based approach to treat advanced breast cancers.

2. Brief Description of the Background Art

Approximately 2000 sequence-specific transcription factors are encoded in the human genome, including ~800 $C_2H_2$-type (Krüppel-like) zinc finger proteins (ZNFs) (1). About half of these ZNFs contain the highly conserved KRAB (Krüppel-Associated Box) repression domain (2, 3). KRAB-ZNFs and their co-repressor KAP1 have co-appeared in evolution of vertebrate organisms starting in tetrapods (4). KRAB-ZNFs underwent unprecedented expansion in mammalian genomes, and KRAB motif represents one of the most rapidly evolving domains (5). Despite the large size of this family, only a few KRAB-ZNFs have been studied in sufficient detail to establish their biological and molecular functions (6-9).

Most KRAB-ZNFs adopt simple protein architecture where the conserved N-terminal KRAB domain is linked with the sequence-specific DNA binding domain comprised of tandem arrays of the $C_2H_2$ type zinc fingers (2, 10). At the molecular level, the KRAB domain directly binds to KAP1, and this interaction is essential for KRAB-ZNFs-mediated repression (11, 12). KAP1 is recruited to chromatin by KRAB-ZNFs (6, 13), and in turn functions as a scaffolding protein for histone- and DNA-modifying enzymes involved in establishing the silenced state of a gene (14, 15). In this process, KAP1 acts as an E3 SUMO ligase and undergoes auto-SUMOylation, which promotes its interaction with the repression machinery (16, 17).

Genetic knockout of KAP1 has revealed its multifaceted role in many organismal processes such as development, reproduction and immune response. KAP1 is essential for differentiation of mouse stem cells in vivo (18, 19). Although the role of KAP1 in development could be attributed to the establishment of imprinting methylation patterns (19, 20) and the control of endogenous retroviral elements (7, 21), its function in adult tissues appears to be distinct (21-23).

KAP1 is a ubiquitously expressed nuclear protein, and its role in cancer is just beginning to emerge. Analysis of tissue microarrays demonstrated that KAP1 expression is increased during the clinical progression of 39% of invasive breast carcinomas in situ to metastasis in lymph nodes (24). High KAP1 mRNA expression has been found to be an independent prognostic factor for peritoneal carcinomatosis (25). Given the relevance of developmental cell fate regulators and stem cell pluripotency to cancer pathogenesis, understanding how KAP1 functions in cancer cells might be critical for developing future therapeutic strategies.

Overexpression of specific KRAB-ZNF genes in cancer has been documented (10). Several KRAB-ZNFs have been implicated in regulation of oncogenes and tumor suppressors in cell culture models, including p53 (26), MDM2 (27), Rb (28), BRCA1 (29) and pVHL (30). In breast cancer, three KRAB-ZNFs undergo gene amplification (31). High expression of 18 KRAB-ZNF genes have been associated with increased resistance of GIST tumors to imatinib treatment (32). However, the expression patterns and functions of the majority of KRAB-ZNFs in breast cancer are still unknown.

In the present invention, we show that KAP1 and certain KRAB-ZNFs are frequently overexpressed in breast tumors at both mRNA and protein levels. Knockdown of KAP1 in breast cancer cells led to inhibition of cell proliferation, tumor growth and metastasis. Mechanistically, we show that KAP1 depletion results in decreased expression of multiple KRAB-ZNF proteins and deregulation of many cancer and metastasis-associated genes. These findings demonstrate that KAP1 and KRAB-ZNFs play an important role in breast cancer and are targets for therapeutic intervention.

SUMMARY OF THE INVENTION

The present invention provides a purified antibody comprising a pan-ZNF specific antibody. Preferably, this purified antibody is a zinc finger linker antibody. More preferably, this purified antibody recognizes (or detects) a conserved zinc finger linker sequence of TGEKPY (SEQ ID NO:1). In another embodiment of this invention, the purified antibody recognizes (or detects) a conserved zinc finger linker sequence of TGEKPY[K/E] (SEQ ID NO: 2/SEQ ID NO: 3). As used herein, the sequence TGEKPY[K/E] (SEQ ID NO: 2/SEQ ID NO: 3) refers to the sequence of TGEKPYK (SEQ ID NO:2) or the sequence of TGEKPYE (SEQ ID NO:3). Other embodiments of this invention include a purified zinc finger linker antibody that recognizes a zinc finger linker sequence of H[Q/K/E]RIHTGEKPY[K/E] (SEQ ID NOS:4-9). As used herein, the term h[Q/K/E]RIHTGEKPY[K/E] (SEQ ID NOS: 4-9) refers to sequences HQRIHTGEKPYK (SEQ ID NO: 4), HQRIHTGEKPYE (SEQ ID NO: 5), HKRIHTGEKPYK (SEQ ID NO: 6), HKRIHTGEKPYE (SEQ ID NO: 7), HERIHTGEKPYK (SEQ ID NO: 8), and HERIHTGEKPYE (SEQ ID NO: 9), respectively. For example, SEQ ID NO:4 is the sequence HQRIHTGEKPYK (SEQ ID NO: 4). In another preferred embodiment of this invention, this purified antibody recognizing these sequences, as set forth herein, connects two adjacent zinc fingers of a protein. The purified antibody of detects multiple ZNF proteins. The purified antibody detects a ZnFL specific signal of cancerous cells. The cancerous cells are cells preferably selected from the group consisting of breast, lung, liver, gastric, and prostate tumors. More preferably, the cancerous cells are one or more breast cancer cells.

The purified zinc finger linker antibody(ies) of this invention, as described herein, is/are capable of binding to a zinc finger linker conserved sequence of TGEKPY (SEQ ID NO:1). Further, the purified zinc linker antibody(ies), as described herein, is/are capable of binding to a zinc finger linker sequence selected from the group consisting of SEQ ID NO:1, SEQ ID NO:2, SEQ ID NO:3, SEQ ID NO:4, SEQ ID NO:5, SEQ ID NO:6, SEQ ID NO: 7, SEQ ID NO:8, and SEQ ID NO:9.

In another embodiment of this invention, a method is provided of treating a patient having cancer comprising administering an effective amount of a purified pan-ZNF specific antibody to the patient. The method of includes wherein the purified antibody is a zinc finger linker antibody. Preferably, the method, as described herein, includes wherein the purified antibody recognizes a conserved zinc finger linker sequence of TGEKPY[K/E] (SEQ ID NO: 2/SEQ ID NO: 3). In this method, the sequence of the purified antibody connects two adjacent zinc fingers of a protein. In a most preferred embodiment of this method, the purified antibody recognizes a conserved zinc finger linker sequence of TGEKPY (SEQ ID NO: 1). The cancerous cell being detected is for example, but not limited to, at least one cell selected from a breast cancer cell, a liver cancer cell, a lung cancer cell, a gastric cancer cell, and a prostate cancer cell. Preferably, the cancerous cell is a breast cancer cell.

In another embodiment of this invention, a diagnostic kit comprising a purified pan-ZNF specific antibody is provided. The diagnostic kit includes wherein the purified antibody is a zinc finger linker antibody. Preferably, the purified antibody detects a conserved zinc finger linker sequence of TGEKPY[K/E] (SEQ ID NO: 2/SEQ ID NO: 3). The diagnostic kit includes wherein the sequence of the purified antibody connects two adjacent zinc fingers of a protein. In a most preferred embodiment of the diagnostic kit, as described herein, the purified antibody detects a conserved zinc finger linker sequence of TGEKPY (SEQ ID NO: 1). The purified antibody detects multiple ZNF proteins. The purified antibody detects a ZnFL specific signal of cancerous cells. The cancerous cells being detected is, for example, but not limited to, at least one cancerous cell selected from a breast cancer cell, a liver cancer cell, a lung cancer cell, a gastric cancer cell, and a prostate cancer cell. Preferably, the cancerous cell being detected is at least one breast cancer cell.

In another embodiment of this invention, an affinity matrix is provided comprising a purified pan-ZNF specific antibody. Preferably, the affinity matrix includes the purified antibody that recognizes or detects a conserved zinc finger linker sequence of TGEKPY[K/E] (SEQ ID NO: 2/SEQ ID NO: 3). The sequence of the purified protein of the affinity matrix connects two adjacent zinc fingers of a protein. In a most preferred embodiment of this invention, the affinity matrix includes wherein the purified antibody recognizes or detects a conserved zinc finger linker sequence of TGEKPY (SEQ ID NO: 1). The purified antibody detects multiple ZNF proteins. The purified antibody detects a ZnFL specific signal of cancerous cells. The cancerous cells is, for example, but not limited to, at least one cell selected from the group of a breast cancer cell, a liver cancer cell, a lung cancer cell, a gastric cancer cell, and a prostate cancer cell. Preferably, the cancerous cell is one or more breast cancer cell.

In another embodiment, a method of detecting cancerous cells comprising subjecting a cancerous cell to a purified pan-ZNF specific antibody, wherein said antibody targets and detects said cancerous cell. Preferably, this method includes wherein the purified pan-ZNF specific antibody recognizes or detects a conserved zinc finger linker sequence of TGEKPY[K/E] (SEQ ID NO: 2/SEQ ID NO: 3). The purified antibody connects two adjacent zinc fingers of a protein. In a most preferred embodiment of this method, the purified pan-ZNF antibody recognizes or detects a conserved zinc finger linker sequence of TGEKPY (SEQ ID NO: 1). The cancerous cells being detected is, for example, but not limited to, at least one cell selected from the group of a breast cancer cell, a liver cancer cell, a lung cancer cell, a gastric cancer cell, and a prostate cancer cell. Preferably, the cancerous cell is one or more breast cancer cells.

In another embodiment of this invention, a pharmaceutical composition is provided comprising a purified zinc finger linker antibody. Preferably, the purified antibody recognizes a conserved zinc finger linker sequence of TGEKPY (SEQ ID NO: 1). Other embodiments of this invention provide a pharmaceutical composition comprising a purified zinc finger linker antibody that recognizes a conserved zinc finger linker sequence of TGEKPY[K/E] (SEQ ID NO: 2/SEQ ID NO: 3).

In another embodiment of this invention, an antigen is provided that is capable of binding to a purified zinc finger linker antibody sequence selected from the group consisting of: SEQ ID NO:1, SEQ ID NO:2, SEQ ID NO:3, SEQ ID NO:4, SEQ ID NO:5, SEQ ID NO:6, SEQ ID NO: 7, SEQ ID NO:8, and SEQ ID NO:9. It will be understood by those person skilled in the art that SEQ ID NOS:3-9 each contain the consensus sequence TGEKPY (SEQ ID NO: 1).

BRIEF SUMMARY OF THE DRAWINGS

Figure Legends

FIG. 9, KRAB-ZNF proteins contain multiple copies of the zinc finger linker (ZnFL) motif. Alignment of linker sequences between zinc fingers from three randomly selected human KRAB-ZNF proteins. Each line contains two histidines (H) from the preceding zinc finger and two cysteines (C) from the following zinc finger shaded in grey. Highly conserved zinc finger linker TGEKPY (SEQ ID NO: 1) residues are shown.

FIG. 12. KAP1 is overexpressed in human breast cancer. Microarray analyses of Trim28/KAP1 expression in four different breast datasets from Oncomine.com.

[1] Herschkowitz J I, Simin K, Weigman V J, Mikaelian I, Usary J, Hu Z, et al. Identification of conserved gene expression features between murine mammary carcinoma models and human breast tumors. Genome biology. 2007; 8:R76

Figure 14:
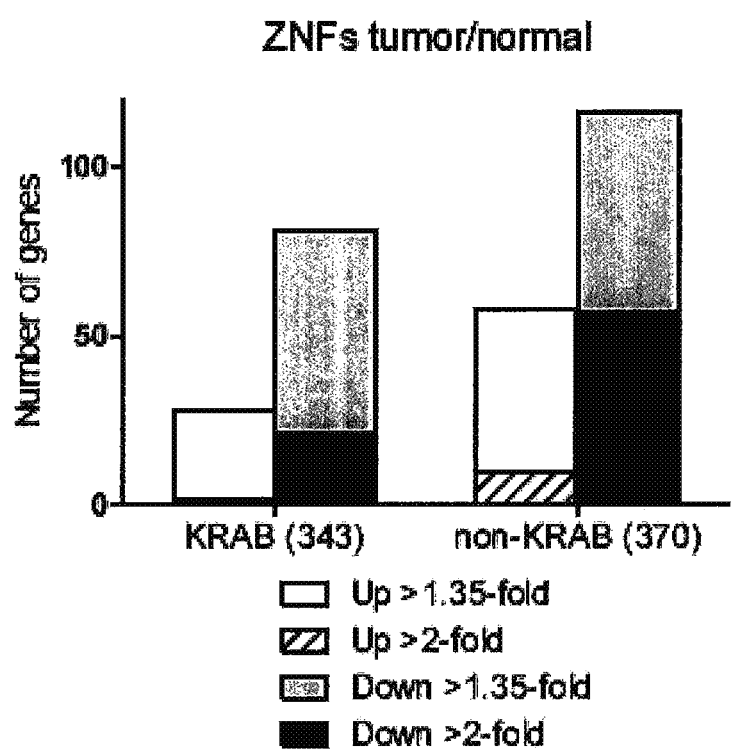

FIG. 14. KRAB-ZNFs and non-KRAB-ZNFs are overexpressed in breast tumors. Expression analysis of 343 KRAB-ZNF and 370 non-KRAB-ZNF genes in TCGA RNA-Seq (n=896) dataset from Supplementary File 1. For all genes $P<0.05$, two-tailed t test.

Figure 15:
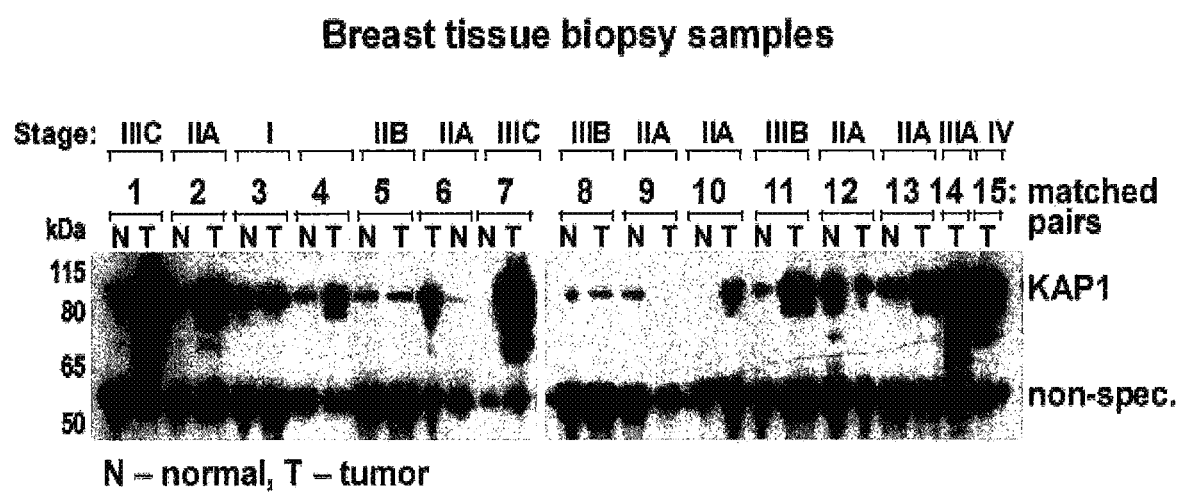

FIG. 15. KAP1 protein is overexpressed in human breast tumors. Western blot analysis of KAP1 protein expression in biopsy samples of matched normal (N)-tumor (T) pairs obtained from the same patients. Stages of breast cancers are shown above. Non-specific band serves as loading control.

Figure 16:
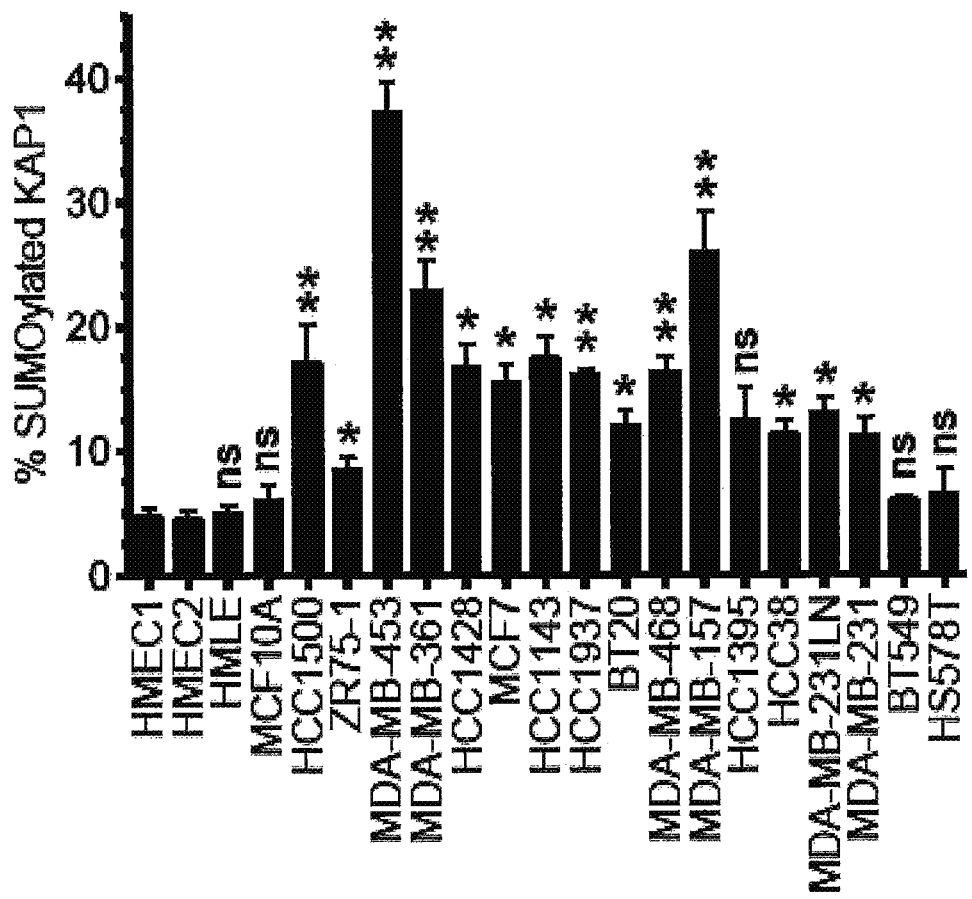

FIG. 16. KAP1 SUMOylation level is increased in breast cancer cell lines. Percentage of SUMOylated KAP1 relative to total KAP1 protein level in each cell line based on densitometric quantification of protein bands from FIG. 3B. Data shown as mean±SD. ns—non-significant, *-$P<0.05$, **-$P<0.01$, two-tailed t test.

Figure 17:
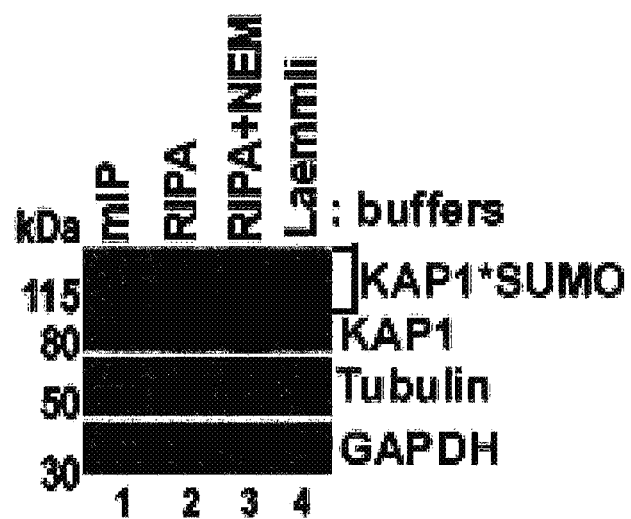

FIG. 17. KAP1 SUMO modification is preserved by N-ethylmaleimide (NEM) and SDS. Western blot analysis of KAP1 in MDA-MB-453 cells lysed in different buffer conditions (mIP—no SDS, RIPA—0.1% SDS, Laemmli—2% SDS). An inhibitor of de-SUMOylating enzymes, NEM was added to lysis buffer to final concentration 10 mM. GAPDH and Tubulin serve as loading controls.

Figure 18:
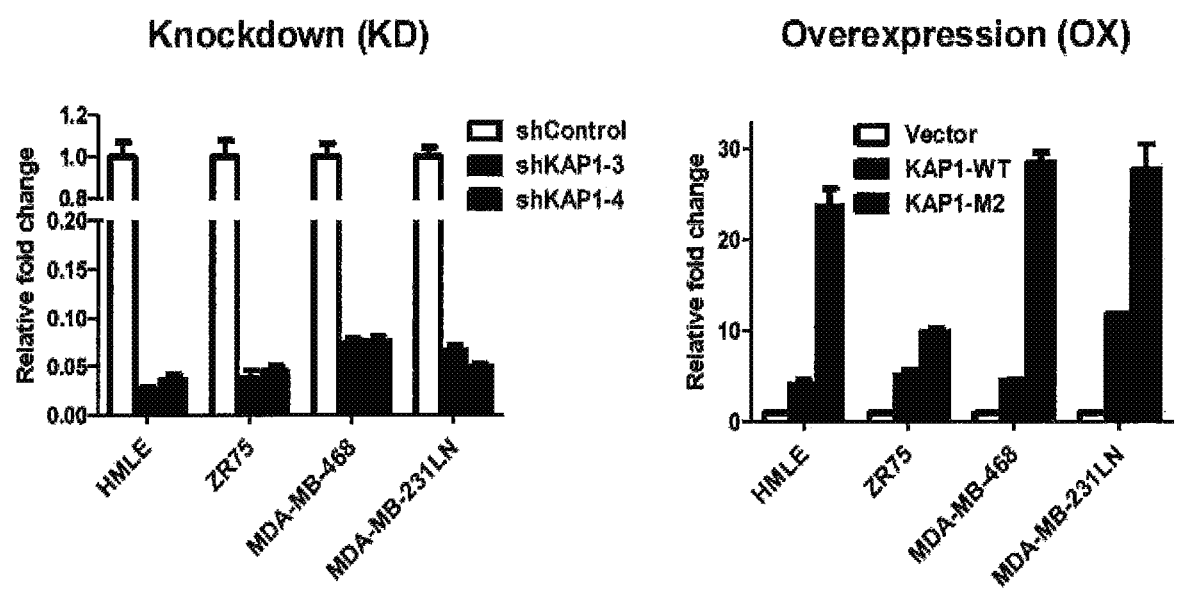

FIG. 18. Extent of KAP1 knockdown and overexpression. RT-qPCR analysis of KAP1 mRNA in the indicated cell lines from FIG. 4A and FIG. 6. KAP1 mRNA levels for controls were assigned the relative value of 1. Data shown as mean±SEM. In all cell lines KD and OX compared to control P<0.001, two-tailed t test.

Figure 19:
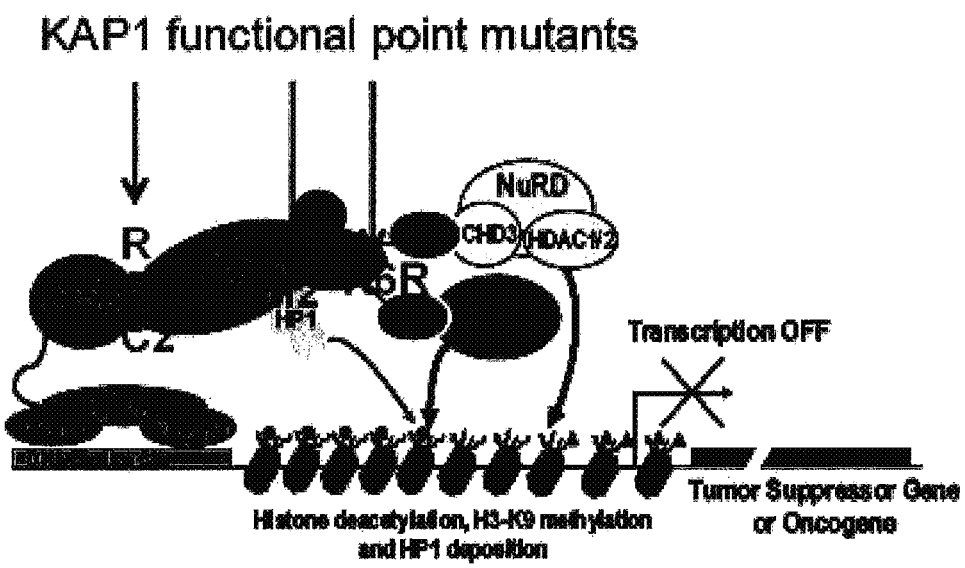

FIG. 19. Schematic representation of KAP1 functional mutants. A model for sumoylation-dependent, KAP1-mediated gene silencing. The SUMO-conjugated KAP1 recruits the NuRD complex and SETDB1 through SUMO interactions, which results in the deacetylation of histones and the methylation of histone H3-K9. KAP1-bound HP1 recognizes H3-K9 methylation. Point mutations were introduced in KAP1 at three separate regions which hinder specific KAP1 interactions. KAP1-R, KAP1-B2 and KAP1-C2 mutants are deficient in KRAB domain binding, KAP1-M2 mutant is deficient in interaction with HP1 and KAP1-K6R mutant is deficient in SUMOylation. Small triangle, acetyl mark; small circle, H3-K9 trimethyl mark on histone tails.

Figure 20:
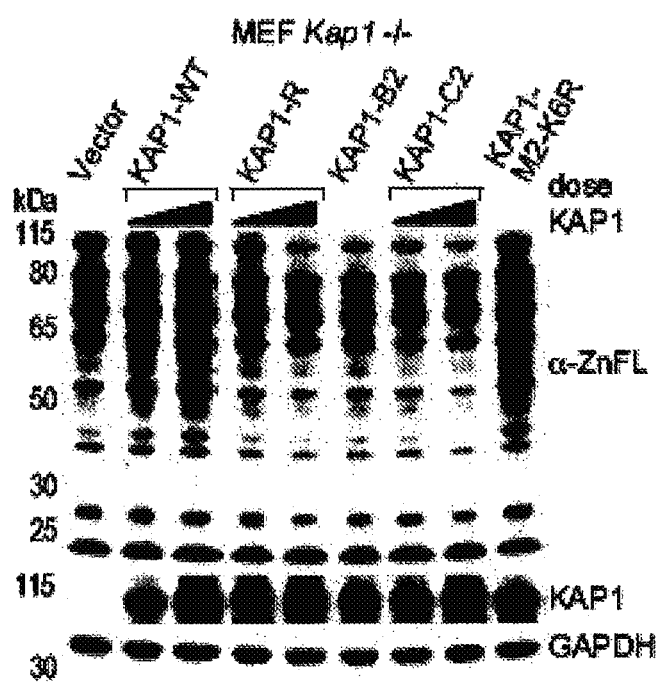

FIG. 20. Expression of KRAB-ZNF proteins depends on their ability to interact with KAP1. WB analysis of KAP1 and KRAB-ZNFs in Kap1 –/– MEFs transfected with vector, wild type KAP1 and the indicated KAP1 mutants. Increasing doses of KAP1 expression constructs were used as shown. GAPDH serves as loading controls. WT—wild type KAP1. R, B2 and C2 are three KAP1 RBCC domain mutants defective in interaction with the KRAB domain. R mutant—RING domain mutation CC65,68AA; B2 mutant—Box2 domain mutation C209A, H212A and C2 mutant—coiled-coil mutation L306P (ref 40). M2-K6R double mutant is defective in HP1 interaction and SUMOylation (both required for transcriptional repression) but capable of binding to the KRAB domain.

Figure 21:
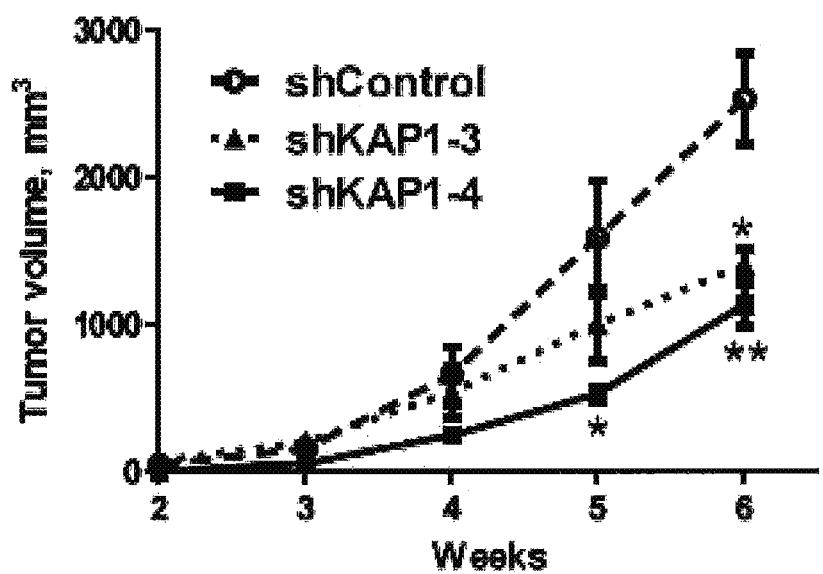

FIG. 21. KAP1 knockdown in MDA-MB-231LN cells inhibits primary tumor growth in orthotopic xenograft mouse model. Tumor growth curves of orthotopically injected MDA-MB-231LN cells: shControl (n=6), shKAP1-3 (n=5), shKAP1-4 (n=5). Data shown as mean+ SEM, *-P<0.05, **-P<0.01, two-tailed Student's t test.

DETAILED DESCRIPTION OF THE INVENTION

As used herein, the term "patient" means members of the animal kingdom, including but not limited to, human beings.

As used herein, the term "having cancer" means that a patient has been diagnosed with cancer.

As used herein, the term "therapeutically effective amount" refers to that amount of any of the present compounds that is required to bring about a desired effect in a patient. The desired effect will vary depending on the illness being treated. For example, the desired effect may be reducing tumor size, destroying cancerous cells, and/or preventing metastasis, any one of which may be the desired therapeutically effective response. On its most basic level, a therapeutically effect amount is that amount needed to inhibit the mitosis of a cancerous cell.

The present invention may be understood more readily by reference to the following detailed description of preferred embodiments of the invention and the methods included therein. Before the present methods and techniques are disclosed and described, it is to be understood that this invention is not limited to specific analytical or synthetic methods as such may, of course, vary. It is also to be understood that the terminology used herein is for the purpose of describing particular embodiments only and is not intended to be limiting. Unless defined otherwise, all technical and scientific terms used herein have the meaning commonly understood by one of ordinary skill in the art to which this invention belongs.

As used herein and in the claims, the singular forms "a," "and," and "the" include plural reference unless the context clearly dictates otherwise. Thus, for example, reference to "a biomarker" is reference to one or more biomarkers and includes equivalents thereof known to those skilled in the art.

The term "antibody," as used herein, refers to immunoglobulin molecules and immunologically active portions of immunoglobulin molecules. As such, the term antibody can refer to any type, including for example IgG, IgE, IgM, IgD, IgA and IgY, any class, including for example IgG1, IgG2, IgG3, IgG4, IgA1 and IgA2 or subclass of immunoglobulin molecules. Further, the terms "antibody" and immunoglobulin" can be used interchangeably throughout the specification. Antibodies or immunoglobulins can be used to encompass not only whole antibody molecules, but also antibody multimer, antibody fragments as well as variants of antibodies, antibody multimers and antibody fragments. Antibodies and immunoglobulins of the invention can be used for various purposes.

The term "diagnosis" refers to methods by which one skilled in the art can estimate and/or determine whether or not a patient is suffering for, or is at some level of risk of developing, a given disease or condition. The skilled artisan, clinician or point of care physician, often makes a diagnosis on the basis of one or more diagnostic indicators, i.e., a biomarker, the risk, presence, absence, or amount of which is indicative of the presence, severity, or absence of the condition. By the terms "detect," "detection," "detectable," "detectable response" and "detecting" are intended to refer to the identification of the presence, absence, or quantity of a given antibody or antigen of this invention.

As used herein, the terms "biological sample," "patient sample" or "sample" refer to a sample obtained from an organism or from components (e.g., cells) of a subject or patient for the purpose of diagnosis, prognosis, or evaluation of subject of interest. In certain embodiments, such a sample may be obtained for the purpose of determining the outcome of an ongoing condition or the effect of a treatment regimen on a condition. The sample may be of any biological tissue or fluid. The sample may be a clinical sample which is a sample derived from a patient. Such samples include, but are not limited to, breast cells, liver cells, lung cells, and cells from among other body tissue samples. Preferably, the sample is at least one cell from breast tissue. Samples may also include sections of tissues such as frozen sections taken for histological purposes.

The present invention provides a purified antibody comprising a pan-ZNF specific antibody. Preferably, this purified antibody is a zinc finger linker antibody. More preferably, this purified antibody recognizes a conserved zinc finger linker sequence of TGEKPY (SEQ ID NO:1). In another preferred embodiment of this invention, this purified antibody of this sequence connects two adjacent zinc fingers of a protein. In another embodiment of this invention, the purified antibody recognizes a conserved zinc finger linker sequence of TGEKPYK (SEQ ID NO:2) or TGEKPYE (SEQ ID NO:3). The purified antibody detects multiple ZNF proteins. The purified antibody detects a ZnFL specific signal of one or more cancerous cells. The cancerous cells are, for example but not limited to, cells of breast, lung, liver, gastric, and prostate tumors. Preferably, the cancerous cells are at least one or more cells selected from the group consisting of breast, lung, liver, gastric, and prostate tumors. Preferably, the cancerous cell is one or more breast cancer cells.

Those persons skilled in the art will understand that the antibody of this invention recognizes or detects consensus sequence TGEKPY (SEQ ID NO: 1) found in zinc finger linkers of human (and mammalian) C2H2-type zinc finger proteins. It will be understood that TGEKPY (SEQ ID NO: 1) is a one-letter code for the six amino acids Threonine-Glycine-Glutamic acid-Lysine-Proline-Tyrosine. The one letter symbols (code) for amino acids are known by those persons skilled in the art. The Materials and Methods section of this application set forth that the actual peptide sequences used for antibody production is H[Q/K/E]RIHTGEKPY[K/E] (SEQ ID NOS: 4-9). The longer peptide provides for efficient immunization. The core consensus TGEKPY (SEQ ID NO: 1) (or TGEKPYK (SEQ ID NO:2), or TGEKPYE (SEQ ID NO:3)) of this invention is specifically found between adjacent C2H2-type zinc fingers. Those persons skilled in the art understand that antibody production is generally a relatively standard and routine procedure. The antibody production is set forth herein. The antibody of this invention of this invention is useful in immunoprecipitation and subsequent protein quantification. The antibody of this invention is useful in applications of Western blotting, immunoprecipitation, immunofluorescence, immunohistochemistry, ELISA, etc., to name a few.

The purified zinc finger linker antibody(ies) of this invention, as described herein, is/are capable of binding to at least one of a zinc finger linker conserved sequence of: TGEKPY (SEQ ID NO: 1), TGEKPYK (SEQ ID NO: 2), and TGEKPYE (SEQ ID NO: 3). Further, the purified zinc linker antibody(ies), as described herein, is/are capable of binding to a zinc finger linker sequence selected from the group consisting of SEQ ID NO:1, SEQ ID NO:2, SEQ ID NO:3, SEQ ID NO:4, SEQ ID NO:5, SEQ ID NO:6, SEQ ID NO: 7, SEQ ID NO:8, and SEQ ID NO:9.

In another embodiment of this invention, a method is provided of treating a patient having cancer comprising administering an effective amount of a purified pan-ZNF specific antibody to said patient. The method of includes wherein the purified antibody is a zinc finger linker antibody. Preferably, the method, as described herein, includes wherein the purified antibody recognizes or detects a conserved zinc finger linker sequence of TGEKPY (SEQ ID NO: 1). In this method, the sequence of the purified antibody connects two adjacent zinc fingers of a protein. In another preferred embodiment of this method, the purified antibody recognizes or detects a conserved zinc finger linker sequence of TGEKPY[K/E] (SEQ ID NO:2/SEQ ID NO: 3). Preferably, the cancerous cell being detected is at least one cell selected from the group consisting of a breast cancer cell, a liver cancer cell, a lung cancer cell, a gastric cancer cell, and a prostate cancer cell.

In another embodiment of this invention, a diagnostic kit comprising a purified pan-ZNF specific antibody is provided. The diagnostic kit includes wherein the purified antibody is a zinc finger linker antibody. Preferably, the purified antibody detects or recognizes a conserved zinc finger linker sequence of TGEKPY (SEQ ID NO: 1). The diagnostic kit includes wherein the sequence of the purified antibody connects two adjacent zinc fingers of a protein. In another embodiment of the diagnostic kit, as described herein, the purified antibody detects or recognizes a conserved zinc finger linker sequence of TGEKPY[K/E] (SEQ ID NO: 2/SEQ ID NO: 3). The purified antibody detects multiple ZNF proteins. The purified antibody detects a ZnFL specific signal of cancerous cells. The cancerous cells being detected is, for example, but limited to at least one cell selected from the group of a breast cancer cell, a liver cancer cell, a lung cancer cell, a gastric cancer cell, and a prostate cancer cell.

In another embodiment of this invention, an affinity matrix is provided comprising a purified pan-ZNF specific antibody. Preferably, the affinity matrix includes the purified antibody that recognizes a conserved zinc finger linker sequence of TGEKPY (SEQ ID NO: 1). The sequence of the purified protein of the affinity matrix connects two adjacent zinc fingers of a protein. In another embodiment of this invention, the affinity matrix includes wherein the purified antibody recognizes a conserved zinc finger linker sequence of TGEKPY[K/E] (SEQ ID NO: 2/SEQ ID NO: 3). The purified antibody detects multiple ZNF proteins. The purified antibody detects a ZnFL specific signal of cancerous cells. The cancerous cells is, for example but not limited to, at least one cell selected from the group of a breast cancer cell, a liver cancer cell, a lung cancer cell, a gastric cancer cell, and a prostate cancer cell.

In another embodiment, a method of detecting cancerous cells comprising subjecting a cancerous cell to a purified pan-ZNF specific antibody, wherein said antibody targets and detects said cancerous cell, is provided. Preferably, this method includes wherein the purified pan-ZNF specific antibody recognizes or detects a conserved zinc finger linker sequence of TGEKPY (SEQ ID NO: 1). The purified antibody connects two adjacent zinc fingers of a protein. In another embodiment of this method, the purified pan-ZNF antibody recognizes or detects a conserved zinc finger linker sequence of TGEKPY[K/E] (SEQ ID NO: 2/SEQ ID NO: 3). The cancerous cells being detected is, for example but not limited to, at least one cell selected from the group of a breast cancer cell, a liver cancer cell, a lung cancer cell, a gastric cancer cell, and a prostate cancer cell.

In another embodiment of this invention, a pharmaceutical composition is provided comprising a purified zinc finger linker antibody. Preferably, the pharmaceutical composition of this invention comprises a purified zinc finger antibody recognizing a conserved zinc finger linker sequence of TGEKPY (SEQ ID NO: 1). In another embodiment of this invention, a pharmaceutical composition is provided comprising a purified zinc finger linker antibody recognizing a conserved zinc finger linker sequence of TGEKPY[K/E] (SEQ ID NO: 2/SEQ ID NO: 3).

In another embodiment of this invention, an antigen capable of binding to a purified zinc finger linker antibody sequence selected from the group consisting of: SEQ ID NO:1, SEQ ID NO:2, SEQ ID NO:3, SEQ ID NO:4, SEQ ID NO:5, SEQ ID NO:6, SEQ ID NO: 7, SEQ ID NO:8, and SEQ ID NO:9, is provided.

The present invention describes a novel diagnostic tool for the evaluation of Zinc finger Factor (ZNF) proteins utilizing a specific antibody described as the pan-Zinc Finger Linker (ZnFL) antibody. In a preferred embodiment, the invention provides a purified ZnFL antibody having a unique structural feature that is common in almost all C2H2-type (Kruppel-like factors) ZNF's; a short, conserved zinc finger linker sequence (TGEKPY[K/E]) (SEQ ID NO:2/SEQ ID NO: 3) that connects two adjacent zinc fingers. This sequence was found to be present in each ZNF protein. Hence, it provides an epitope or an anti-body specific region on which to bind. By isolating this ZnFL antibody, it was tested and found to be potent and efficient in recognizing and detecting multiple ZNF's. These tests open up the possibilities of studying human ZNF transcription factors.

The relationship between the transcriptional regulator, KAP1 and a Zinc finger Factor, 'Kruppel Associated Box' (KRAB)-ZNF is discussed herein. It was discovered that certain breast cancers and breast cancer cell-lines had overexpressed KAP1 and KRAB-ZNF. Consequently, a reduction in expression of the KRAB-ZNF or the knock-down of KAP1 resulted in "down regulation of genes linked to tumor progression and metastasis. This result clearly demonstrates that KAP1 is a regulator of KRAB-ZNF proteins as well as an important factor in breast cancer research.

The transcriptional regulator TRIM28/KAP1 plays an important role in development, stem cell self-renewal, chromatin organization and the DNA damage response. KAP1 is an essential co-repressor for KRAB zinc finger proteins (KRAB-ZNFs). Though KRAB-ZNFs represent the largest family of human transcription factors, their biological functions are largely unknown. Using the conserved zinc fingers linker region (ZnFL) as antigen, we have developed a ZnFL antibody that recognizes multiple KRAB-ZNFs. We showed that KAP1 and many KRAB-ZNFs were overexpressed in human breast cancers and breast cancer cell lines. In addition, an active SUMOylated form of KAP1 was markedly increased in breast cancer cells. Furthermore, KAP1 depletion in breast cancer cell lines reduced cell proliferation and inhibited tumor growth and metastasis of tumor xenografts. Conversely, KAP1 overexpression stimulated cell proliferation and tumor growth. KAP1 knockdown led to down-regulation of genes previously linked to tumor progression and metastasis, including EREG/epiregulin, PTGS2/COX2, MMP1, MMP2 and CD44. Interestingly, KAP1 depletion or genomic deletion led to dramatic down-regulation of multiple KRAB-ZNF proteins due in part to their increased degradation. KAP1-dependent stabilization of KRAB-ZNFs required a direct KRAB-ZNF-KAP1 interaction. These results establish KAP1 as a positive regulator of multiple KRAB-ZNFs and an important factor in the development of breast cancer.

Out of approximately 2000 sequence specific transcription factors within the human genome, about 800 are described as C2H2-type (Kruppel-like) zinc finger factors (ZNF). However, the detection and analysis of these factors is difficult due to their low expression levels and the unavailability of potent and specific antibodies. Previous analysis of multiple ZNF proteins has not been possible due to a lack of antibodies for the detection of these proteins. Furthermore, generating specific antibodies for each of the approximately 800 ZNF proteins would be highly inefficient and extremely expensive. The invention describes the unique structural feature of the ZNF proteins: a short, conserved zinc finger linker sequence that connects two adjacent zinc fingers. The purified antibody of this invention achieves detection at high sensitivity and broad specificity to the majority of ZNF's. The innovative advantages of this invention is as follows: high sensitivity and the ability to detect endogenous levels of ZNF proteins; the ability to analyze multiple ZNF proteins simultaneously; and the ability to isolate (affinity purify) and enrich the ZNF proteome for further analysis.

This invention provides a purified antibody comprising a pan-ZNF specific antibody. Preferably, this purified antibody is a zinc finger linker antibody. More preferably, this purified antibody recognizes a conserved zinc finger linker sequence of TGEKPY (SEQ ID NO: 1). This sequence connects two adjacent zinc fingers of a protein. Another embodiment of this invention provides a purified antibody having a conserved zinc finger linker sequence of TGEKPY[K/E] (SEQ ID NO: 2/SEQ ID NO: 3). The purified antibodies of this invention detect multiple ZNF proteins. The purified antibodies of this invention detect a ZnFL specific signal of cancerous cells. The cancerous cells include breast cancer cells. Other embodiments of this invention provide a method of detecting cancerous cells comprising subjecting a cancerous cell to a purified pan-ZNF specific antibody, wherein the antibody targets and detects the cancerous cell. Another embodiment of this invention provides for a method of treating a patient having cancer comprising administering an effective amount of a purified pan-ZNF specific antibody to the patient. Another embodiment of this invention provides for a diagnostic kit comprising a purified pan-ZNF specific antibody. Yet another embodiment of this invention provides an affinity matrix comprising a purified pan-ZNF specific antibody. The antibody of this invention may be used, for example but not limited to, clinically for effecting the therapeutic treatment of a patient with cancer, as a diagnostic tool, as an immune-precipitation kit, as a protein array, or as an affinity matrix.

Materials and Methods

Generation of ZnFL Antibody

The rabbit polyclonal ZnFL antibody was raised against a mixture of Z1 and Z2 peptides. Z1 (Ac-CGGH[Q/K/E]RIHTGEKPY[K/E]-amide) (SEQ ID NOS: 10-15) and Z2 (Ac-GH[Q/K/E]RIHTGEKPY[K/E]C-amide) (SEQ ID NOS: 16-21) peptides were synthesized and used for rabbit immunization and affinity purification of ZnFL antibody.

Cell Lines and Constructs

Luciferase expressing metastatic subline MDA-MB-231-luc-D3H2LN (MDA-MB-231LN) cells were purchased from Caliper Life Science. Primary HMECs were purchased from Lonza and Invitrogen. HMLE cells were kindly provided by Dr. Robert Weinberg (MIT, Cambridge, Mass.), S2 cells by Dr. Alexei Tulin (FCCC, Philadelphia, Pa.), AB9 and XTC cells by Dr. Neil Hukriede (UPitt, Pittsburgh, Pa.), CEF and MEF cells by Dr. Daniel Flynn (WVU), KAP1 knockout MEFs (21) by Dr. Didier Trono (EPFL, Lausanne, Switzerland). The other cell lines were purchased and authenticated by ATCC. shRNAs were expressed from pTRIPZ vector and induced by addition of 0.5 μm/ml doxycycline for 7 days. FLAG-KAP1 WT and mutants (16) were expressed from pLU vector. ZNF10, 224, 317, 350 were expressed from pcDNA3-6HA.

Cell Proliferation Assay $2 \times 10^4$ cells were plated in triplicates in 6w plates, cultured for 2, 4, 6 and 8 days, trypsinized and counted on Countess (Invitrogen).

Quantitative RT-PCR

Total RNA was extracted using mirVana miRNA Isolation Kit in triplicates. 2 μg of total RNA were reverse transcribed using SuperScriptIII and $dT_{20}$ primer. qPCR was performed in an ABI-7500 Real-Time PCR Cycler and analyzed using ABI SDS2.06 software. Gene expression levels were normalized by the geometrical mean of UBC, RPL13A, PCNA and tubulin genes relative to control. The primers and shRNAs are described in the Supplementary Methods.

Western Blotting and Immunoprecipitation

Cells were lysed in non-reducing Laemmli buffer and total protein was quantified by BCA assay. ProteoJET Cytoplasmic and Nuclear Protein Extraction Kit (Fermentas) was used for subcellular fractionation for FIG. 1C. Lysates with equal amount of total protein were separated on 4-12% Bis-Tris gels and transferred to a PVDF membrane. Protein bands were detected using standard chemiluminescence techniques and quantified by GeneTools software (Syngene). Breast OncoPair INSTA-Blot™ was purchased from Imgenex, cat. IMB130a. Immunoprecipitation was performed in mIP (FIG. 1D) or RIPA buffer (FIG. 1E, 3E) as described (16). The antibodies are described herein.

Animal Studies and Bioluminescence Imaging (BLI)

NOD.Cg-Prkdc$^{scid}$ 112rg$^{tm1Wj1}$/SzJ (NSG) mice were purchased from the Jackson Laboratory and fed doxycycline-containing diet (Bio-Serv) to maintain shRNA expression. Mice were injected with MDA-MB-231LN cells and imaged as described (33). Primary tumor and organs with metastases were collected at the end point of study and analyzed as described (33).

Microarray, Proteomics and Bioinformatics Analyses are Described in the Supplementary Methods.

Cell Lysis and Western Blotting

Cells were lysed in 1XLaemmli gel loading buffer (GLB). Total protein was quantified by BCA protein assay. 2-mercaptoethanol was added to lysates to a final concentration 100 mM. Nuclear-cytoplasmic fractionation was done with ProteoJET Cytoplasmic and Nuclear Protein Extraction Kit (Fermentas). Lysates with equal amount of total protein were separated on Novex 4-12% Bis-Tris gels (Invitrogen) and transferred to a PVDF membrane. Membranes were blocked with 5% non-fat milk in 1×PBS containing 0.05% Tween-20. Protein bands were detected using standard chemiluminescence techniques and quantified by GeneTools software (Syngene). Human Breast OncoPair INSTA-Blot™ was purchased from Imgenex, cat. IMB130a. The antibodies used are described herein.

Immunoprecipiation Analysis

Cells were lysed in mIP buffer (16), cell lysates were pre-cleared with ProteinA/G PLUS-agarose for 1 hr and supernatants transferred into new tubes. 200 µg of total protein were incubated with 2 µg ZnFL antibody or normal rabbit IgG, and with 30 µl of EZview anti-FLAG or anti-HA (Sigma) beads for 4 hours and washed 3 times with 1 ml mIP. Pellets and supernatants were then solubilized in 2XGLB and analyzed by Western blotting.

Animal Studies and Bioluminescence Imaging (BL1)

NOD.Cg-Prkdc$^{scid}$ 112rg$^{tm1Wj1}$/SzJ (NSG) mice were purchased from the Jackson Laboratory (stock 5557) and used at 6-8 weeks of age. To maintain shRNA expression, mice were fed doxycycline-containing chow (Bio-Serv, 200 mg/kg). Mice were injected with luciferase-expressing MDA-MB-231LN cells and imaged weekly after peritoneal injection of ~150 mg/kg D-luciferin. Images were obtained and quantified using the MS Lumina El Imaging System and Living Image 4.0 software (Caliper Life Sciences). 1×10$^6$ cells were injected into the fourth inguinal mammary gland of female mice and followed by BLI for 6 weeks. 2×10$^5$ cells were injected into tail vein of male mice and followed by BLI for 3 weeks. Primary tumor and organs with metastases were collected at the end point of study, fixed in formalin, processed and analyzed in the WVU Department of Pathology using serial sectioning and H&E staining. Tumor volumes were measured by caliper and calculated according to the formula V=0.5236×L×W$^2$ (33).

Protein Sequence Alignments

Raw C$_2$H$_2$ zinc finger protein sequence data were downloaded from (1). The Protein Sequence Motif Extractor, Pacific Northwest National laboratory, Richland, Wash., was used to extract 28 amino acid motifs (X7-C-X2-C-X12-H-X3-H) from the sequences of each species. The results were used for generating Logo figures through a web-based tool WebLogo available from University of California, Berkeley.

Microarray Methods

The RMA-normalized intensities of Affymetrix HuEx-1-st-v2 microarrays were used as indicator of gene expression. Statistical and bioinformatics analysis was conducted using the software packages Partek Genomic Suite. Briefly, after vender-recommended quality control and normalization, the control group was used as a baseline to calculate the log 2-transformed intensity ratio before further statistical analysis. The p-values were obtained by an unpaired t-test assuming unequal variance. False discovery rate p-value correction was conducted for multiple hypothesis testing purpose.

TCGA Data Analysis

Breast TCGA data were downloaded from the Cancer Genome Atlas (TCGA), National Institutes of Health. Statistical programming software R (version 3.0.1) was used to assemble and process the data. Molecular subtyping was accomplished using the Bioconductor 2.12 Genefu R package.

Statistical Analysis

Statistical analyses were performed with Prism5 software (GraphPad) using two-tailed Student's t test.

Results:

Characterization of a ZnFL Polyclonal Antibody

The limited availability of reagents has hindered analysis of KRAB-ZNF proteins to date. Perhaps as few as four antibodies capable of detecting endogenous levels of individual KRAB-ZNF proteins have been reported (6, 34, 35). After testing multiple commercial antibodies to many KRAB-ZNFs, we were able to detect endogenous levels of ZNF192 and ZNF274. Difficulty in detection of KRAB-ZNFs is likely due to their relatively low expression levels, a characteristic of many transcription factors (1). To overcome this problem and to analyze expression of the majority of KRAB-ZNFs simultaneously, we developed a pan-ZNF-specific antibody, referred to as the ZnFL antibody thereof. A unique structural feature of most C$_2$H$_2$-type ZNFs is a short and remarkably conserved zinc finger linker ("ZnFL") sequence, TGEKPYK/E, that connects two adjacent zinc fingers (FIG. 1A). More than 90% of all individual zinc fingers in human C$_2$H$_2$-type ZNFs, including ~350 KRAB-ZNFs, contain this or highly similar sequence (FIG. 9, (4)). The ZnFL is present in each KRAB-ZNF with the frequency typically equal to the number of zinc fingers minus one (FIG. 1B). The median number of zinc fingers in human KRAB-ZNFs is 12 (2), providing multiple ZnFL epitopes in each KRAB-ZNF. Thus the ZnFL antibody of this invention will recognize KRAB-ZNF proteins.

Figure 10:
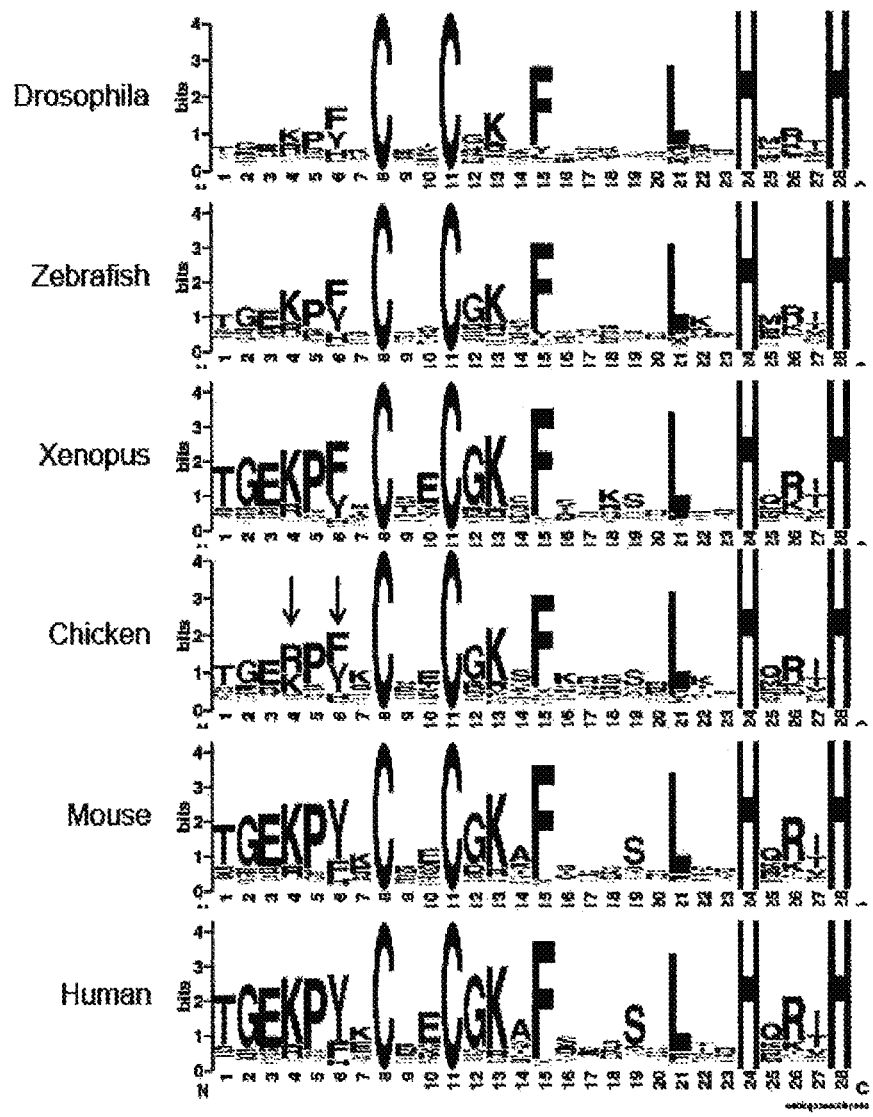
FIG. 10. Zinc finger linker conservation in different species. Logo representation of amino acid conservation in 28-aa zinc finger domains of C2H2-type ZNF proteins from different species. A high bit score reflects invariant residues C, C, H and H. 7-aa zinc finger linker sequence TGEKPY [K/E] (SEQ ID NO: 2/SEQ ID NO: 3) is highly conserved. Arrows show prevalence of R and F in chicken proteins.
Figure 11:
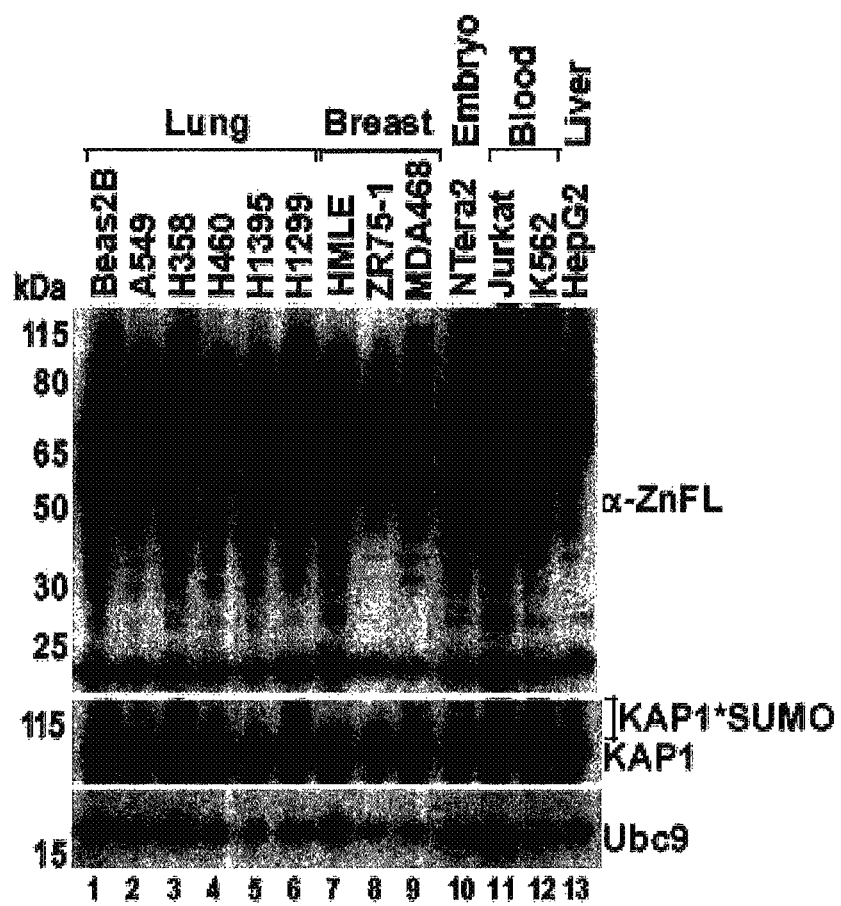
FIG. 11. Ubiquitous expression of KAP1 and ZNFs in human cancer cells lines. Western blot analysis of KAP1 and ZNFs in different human cancer cells lines of lung, breast, embryo, blood and liver origin. Ubc9 serves as loading control.

A rabbit polyclonal ZnFL antibody was raised using ZnFL consensus peptides as antigens, affinity purified and validated by Western blotting (FIGS. 1C and 11). Nuclear and cytoplasmic fractions from cells from several species representing different clades of the eukaryotes were analyzed. As expected, ZnFL antibody did not detect ZNFs in yeast and reacted with only a few proteins in Drosophila cell lysates. However, strong ZnFL-specific signals were observed in the nuclear fractions from all vertebrate cells. The stronger signal in zebrafish lysates is likely due to the tetraploid nature of these cells and a higher content of nuclear proteins as evidenced by the strong histone H3 signal. Interestingly, only three weak ZnFL-reactive bands were detected in chicken cell lysates, suggesting that the avian ZNFs have diverged significantly in the structure of the zinc finger linker. Indeed, alignment of zinc finger sequences across species revealed divergence of the avian sequence from the sequence of other species at the fourth and sixth positions (FIG. 10). ZnFL-reactive protein bands were primarily in the nucleus, consistent with the notion that ZNFs are transcription factors. The monoclonal antibody raised to human KAP1 protein detected KAP1 in human, mouse and Xenopus cells (FIG. 1C). It did not recognize chicken KAP1 likely due to sequence divergence between the species. Consistent with the expected range of sizes for human ZNFs (4), the ZnFL antibody detected multiple protein bands in the range of 40-150 kDa in total cellular lysates from all human cell lines tested (FIG. 11).

The interaction of ZnFL-reactive proteins with KAP1 was confirmed using co-immunoprecipitation (IP). Proteins from human mammary epithelial HMLE cells expressing FLAG-KAP1 were immunoprecipitated with the FLAG or control HA antibody (FIG. 1D). The ZnFL antibody detected many proteins in the FLAG immune complex but not in the control IP. Endogenous KRAB-ZNFs, ZNF192 and ZNF274, were specifically detected in the FLAG immune complex and served as positive controls. Most importantly, IP with FLAG antibody recovered the majority of the ZNF protein bands (FIG. 1D, compare lanes 4 and 8), suggesting that these correspond to ZNFs with the KRAB domain, i.e. KRAB-ZNFs. The reciprocal IP using the ZnFL antibody or control normal rabbit IgG was also performed. As expected, endogenous KRAB-ZNFs, ZNF192 and ZNF274, were present in the ZnFL IP but not the control IP. KAP1 was also detected in the ZnFL immune complex but not the control IP. Further, the ZnFL antibody efficiently precipitated three randomly selected HA-tagged KRAB-ZNFs: ZNF224, ZNF317 and ZNF350 (FIG. 1E), indicating the potential to recognize most KRAB-ZNFs.

The identity of ZnFL antibody-recognized proteins was confirmed by mass spectrometry of control IgG and ZnFL immunoprecipitates. From 37 proteins specific to the ZnFL IP from MDA-MB-231LN breast cancer cells, 22 were ZNFs (Table1) and 15 were abundant non-nuclear contaminants. Both, ZNF192 and ZNF274 are expressed in MDA-MB-231LN cells (FIG. 3B). Absence of ZNF274 in the mass spectrometry data suggested that the identified ZNFs are likely the most abundant or/and amenable to LC-MS/MS and the total number of 22 expressed ZNFs in these cells is an underestimation.

These results clearly demonstrate that ZnFL antibody detects proteins consistent with sequence, expected size, subcellular localization and expression pattern of ZNFs. Notably, the majority of the ZnFL-detected proteins co-immunoprecipitated with KAP1 (FIG. 1D), indicating that significant proportion of ZnFL-recognized bands represent KRAB-ZNFs. Due to their ability to interact with KAP1 (FIG. 1D), most of the ZnFL-detected ZNFs appear to be KRAB-ZNFs. KRAB-ZNFs are preferentially recognized by ZnFL antibody likely due to the fact that they contain on average significantly larger number of zinc fingers per protein compared to non-KRAB ZNFs (2).

KAP1 and KRAB-ZNFs are Overexpressed in Human Breast Tumors

Figure 13:
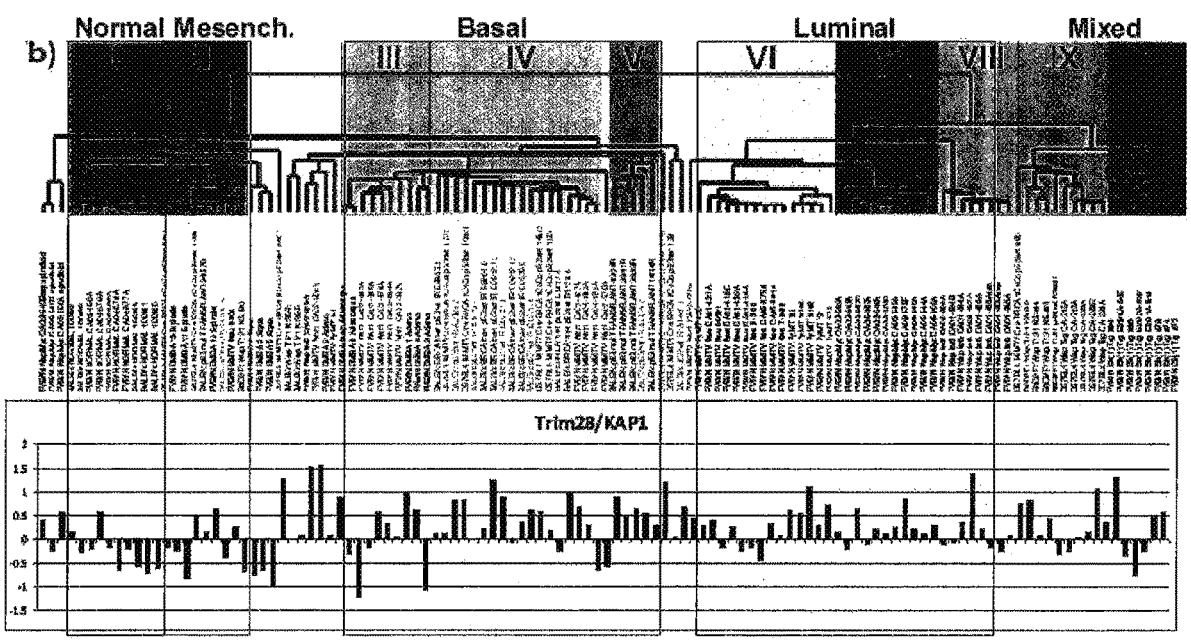
FIG. 13. KAP1 is overexpressed in mouse mammary tumors. Microarray analysis of Trim28/KAP1 expression in 108 tumors from 13 different mouse models of breast cancer. Normalized expression data were downloaded from [1] and plotted for Trim28/KAP1 on log 2-transformed scale. Group assignments are from [1]. Group I represents normal mammary tissue.

TRIM28/KAP1 and KRAB-ZNFs expression in human breast cancer was first analyzed at the mRNA level. KAP1 was modestly overexpressed (1.3-2.1-fold) in breast carcinoma compared to normal tissue in several public array datasets (FIG. 12). KAP1 was up-regulated in TCGA breast tumor data, with 525 samples profiled by Agilent mRNA expression arrays and 896 samples analyzed by RNA-Seq (FIGS. 2A and 12). The KAP1 level was higher in all four intrinsic breast cancer subtypes and in breast cancer metastases (FIGS. 2A and B). Analysis of a mouse dataset comprised of 108 tumors from 13 different mouse models of breast cancer revealed that KAP1 was up-regulated in all molecular tumor subtypes compared to normal tissue, 1.4- fold on average (FIG. 13). KAP1 up-regulation in breast tumors was consistent across multiple datasets but relatively modest in absolute fold change. Noteworthy, the basal level of KAP1 mRNA in normal breast tissue is relatively high and is comparable to the levels of such housekeeping genes as TUBA1A, PCNA and HPRT1.

To determine if KRAB-ZNFs, which utilize KAP1 as a co-repressor, are also overexpressed in breast cancer, we analyzed their expression in the two TCGA breast datasets. Of 365 annotated KRAB-ZNF genes, 343 were detected in the RNA-Seq dataset and 289 in the array dataset. Most KRAB-ZNF genes common for both datasets were regulated in tumors concordantly, though fold changes for up-regulated genes in the RNA-Seq dataset were lower. Thus, 28 genes were up-regulated >1.35-fold in the RNA-Seq dataset and 70 genes in the array dataset, and 48 of the up-regulated genes were common to both datasets (>1.35-fold in at least one dataset, P<0.05 in both). 81 genes were down-regulated >1.35-fold in the RNA-Seq dataset and 70 genes in the array dataset, and 64 down-regulated genes were common to both datasets by the same criteria (FIG. 2C). Only 10 KRAB-ZNF genes were up-regulated in one dataset and down-regulated in the other or vice-versa. Less than a quarter of the differentially regulated KRAB-ZNFs, however, showed changes of more than 2-fold, suggesting that deregulation of rather multiple KRAB-ZNF genes simultaneously but at a modest level occurs in breast tumors. We also analyzed expression of a more diverse superfamily of non-KRAB-ZNF genes and found similar general trend (FIG. 14).

KAP1 protein expression was compared in surgical samples of matched normal-tumor pairs. The vast majority of the tumor samples demonstrated 2-10-fold higher level of KAP1 protein compared to their normal controls (FIGS. 2D and 15). Immunohistochemical analysis has documented elevated KAP1 levels in significant proportions of breast, lung, liver, gastric and prostate tumors (FIG. 2E and see TRIM28 at www.proteinatlas.org), indicating that KAP1 overexpression is a common feature of many epithelial cancers.

To analyze KRAB-ZNF proteins expression in breast tumors, the same matched normal-tumor samples were probed with the ZnFL antibody. Interestingly, substantially higher levels of multiple KRAB-ZNFs were detected in most tumors compared to normal controls, and they correlated with KAP1 protein levels (FIG. 2D). These results indicate that KAP1 and multiple KRAB-ZNFs are frequently overexpressed in breast tumors at the mRNA level, but most profoundly at the protein levels.

KAP1, KAP1 SUMOylation and KRAB-ZNFs are Up-Regulated in Human Breast Cancer Cell Lines Analysis of gene expression in tissue samples is confounded by the complexity of tissue composition made up of multiple cell types and their relative contribution to the sum readout signal. To analyze pure cell populations, we compared KAP1 levels in two independent isolates of primary human mammary epithelial cells (HMECs), two immortalized mammary cell lines, HMLE and MCF10A, and a panel of 17 breast cancer cell lines representing luminal, basal and claudin-low breast cancer subtypes. Similarly to the human patient data, KAP1 mRNA levels were elevated 1.5-3-fold in breast cancer cell lines compared to primary HMECs (FIG. 3A). The highest KAP1 levels were observed in luminal cells.

KAP1 protein was up-regulated in most cancer cell lines by 2-4-fold when normalized to tubulin, with higher levels observed in luminal cells (FIGS. 3B and C). For a comparison, we analyzed expression of established breast cancer oncogenes in the same cells. Interestingly, KAP1 protein was overexpressed at least as often as β-Catenin (36) and more often than c-Met (37) (FIG. 3B).

The most striking difference was detected in the levels of SUMOylated KAP1 (FIGS. 3B, D, and E, and 16). We have previously shown that conjugation of each SUMO moiety to the six SUMOylation sites in KAP1 adds ~15 kDa to the 100 kDa unmodified KAP1 protein and results in the appearance of a ladder of discrete higher molecular weight KAP1-SUMO conjugates (16). SUMO modification of KAP1 can only be detected in cells lysed in buffers containing SDS or NEM, an inhibitor of de-SUMOylating enzymes (FIG. 17, (16)). To confirm that the observed KAP1*S bands represent SUMOylated KAP1, we performed KAP1 IP and WB with SUMO2/3 antibody (FIG. 3E). When calculated as a fraction of total KAP1 signal, levels of SUMOylated KAP1 varied from 4% in HMECs up to 35% in MDA-MB-453 cells, with majority of cancer cell lines within 10-20% range (FIG. 16). When normalized to tubulin, SUMOylated KAP1 was 5-30-fold higher in luminal and basal cancer cell lines compared to HMECs and immortalized cells (FIG. 3D). KAP1 SUMOylation level is an indicator of KAP1 co-repressor activity (16, 17). These results suggest that not only KAP1 level, but also its activity is markedly increased in breast cancer cells.

Most breast cancer cells showed an increase in total ZnFL-specific signal compared to primary HMECs, with higher intensity bands observed in cells of luminal and basal subtypes (FIG. 3B), suggesting that, similarly to KAP1, KRAB-ZNF proteins are broadly up-regulated in breast cancer cell lines. In many cases, we observed higher KRAB-ZNFs signal in cell lines with higher KAP1 level, suggesting that they could be co-regulated. In sum, these results indicate that KAP1 and KRAB-ZNFs expression and KAP1 SUMOylation are significantly elevated in breast cancer cell lines compared to primary cells.

Genomic Alterations of KAP1 and KRAB-ZNFs in Human Breast Tumors

We analyzed frequencies of genomic alterations for KAP1 and all ZNF genes in the TCGA breast dataset. Interestingly, only four missense mutations were identified in KAP1, which are likely passenger mutations. We identified five KRAB-ZNF genes mutated in more than 1% of cases and three of them were also down-regulated in tumors at the mRNA level (ZNF208, ZNF41 and ZNF540). Some of the mutations in these three KRAB-ZNFs were nonsense mutations, while approximately half of the missense mutations were located in the zinc finger DNA binding domain, suggesting that they are likely functionally inactivating mutations.

We identified six KRAB-ZNF genes at three separate loci that have undergone genomic deletions with frequencies between 8.3% and 43.9% of cases, and five of them were also down-regulated in tumors at the mRNA level (ZNF778, ZNF595, ZNF141, ZNF721 and ZNF658), suggesting that these are likely loss-of-function events. We identified a cluster of five KRAB-ZNF genes at 1q44 that has undergone genomic amplification in 45.3% of cases, and three of these genes were also up-regulated in tumors at the mRNA level (ZNF695, ZNF669 and ZNF124), suggesting that these are likely gain-of-function events. In general, non-KRAB-ZNF genes followed similar patterns of mutations and gains/losses to those of KRAB-ZNFs.

These results indicate that a small number of KRAB-ZNF genes are genetically altered in breast cancer. The identified genes should be functionally validated as cancer gene candidates in the future.

KAP1 Positively Regulates the Protein Levels of Multiple KRAB-ZNFs

A positive correlation between KAP1 and KRAB-ZNF protein levels was consistently observed (FIGS. 2D, 3B, and 11). To evaluate if KAP1 controls the expression of KRAB-ZNFs, KAP1 was inhibited using multiple shRNAs in a set of breast cancer cell lines of luminal (ZR75-1), basal (MDA-MB-468) and claudin-low (MDA-MB-231LN) subtypes as well as in 'normal' mammary epithelial cells (HMLE) (FIGS. 4A and 18). Surprisingly, we found that expression of multiple KRAB-ZNF proteins decreased significantly in KAP1-depleted cells and in Kap1 knockout fibroblasts, and conversely increased in cells overexpressing exogenous KAP1. The increase in KRAB-ZNFs levels was also induced by the repression-impaired KAP1 M2 mutant, suggesting that the up-regulation likely occurs at post-transcriptional level (FIG. 4A).

Microarray expression profiling revealed only modest changes in expression of a few KRAB-ZNF genes in KAP1-depleted MDA-MB-231LN cells. Previous microarray experiments conducted in multiple cell lines with KAP1 knockdown or in mouse tissues with Kap1 knockout yielded similar findings—marginal (<2-fold) changes in expression of a limited number of KRAB-ZNFs (22, 23, 38). Furthermore, ZNF192 protein decreased significantly upon KAP1 depletion in HMLE and ZR75-1 cells without changes in ZNF192 mRNA (FIG. 4B). These results suggested that the decrease of multiple KRAB-ZNF proteins following KAP1 knockdown is largely post-transcriptional.

To analyze if KRAB-ZNF proteins are degraded faster in the absence of KAP1, we treated cells with the proteasome inhibitor MG-132. Indeed, the expression level of multiple KRAB-ZNFs was elevated in KAP1-depleted cells following inhibition of proteosomal degradation to the same level as in control cells. The level of ZNF192 protein was similarly rescued (FIG. 4C, compare lanes 2 and 4). At the same time, the levels of KAP1 and control GAPDH proteins decreased slightly (FIG. 4C). These results suggest that KAP1 regulates KRAB-ZNF proteins stability.

Interaction with KAP1 Protects the KRAB-ZNFs from Proteasomal Degradation

KAP1 binds directly to the KRAB domain (12) and can potentially stabilize KRAB-ZNFs through direct protein-protein interaction. In rescue experiments, we infected HMLE shKAP1 cells with lentiviruses expressing shRNA-resistant KAP1 cDNAs. As expected, re-expression of wild type KAP1 resulted in elevated expression of multiple KRAB-ZNFs (FIG. 5A). Expression levels of KRAB-ZNFs were also rescued by reconstitution with KAP1 mutants that are impaired in repression function, i.e. the M2 mutant, which is deficient in interaction with HP1 (39), and the K6R mutant, which is SUMOylation deficient (16) (FIGS. 5A and 19). This result confirmed that KAP1-dependent regulation of KRAB-ZNF protein levels was post-transcriptional. However, re-expression of a KAP1 mutant deficient in KRAB binding, the C2 mutant (16, 40), failed to restore KRAB-ZNFs expression levels, indicating that direct KAP1 binding to the KRAB domain is required for KRAB-ZNFs protein stabilization. We obtained similar results by transfection of KAP1 mutants into Kap1 −/− MEFs (FIG. 20).

In a complementary experiment, two different KRAB-ZNFs (ZNF10/KOX1 and ZNF350/ZBRK1) were transiently transfected into control and KAP1-depleted cells. Both wild type ZNF10 and ZNF350 were expressed at significantly lower levels in KAP1-depleted cells compared to control cells (FIG. 5B), indicating that KRAB-ZNFs expression depends on the level of endogenous KAP1. The difference in KRAB-ZNFs levels was not due to variation in transfection efficiency since the expression of co-transfected GFP was similar in both cell lines. To further establish mechanism, ZNF10 and ZNF350 mutants were analyzed. The DV point mutation (DV→AA) in the KRAB domain impairs interaction with KAP1 and its repression activity (11, 12). The DV mutants were expressed at much lower levels than the corresponding wild type KRAB-ZNFs in control cells, indicating that binding of KRAB-ZNFs to KAP1 is critical for expression. A KRAB-only variant of ZNF10 (KRAB) could be expressed in control cells, but was almost undetectable in the absence of KAP1. Expression of a mutant of ZNF350 lacking the KRAB domain (dK) did not significantly differ between control and KAP1-depleted cells. These results strongly support the conclusion that the presence of the KRAB domain, which is essential for KAP1 binding, is required for efficient KRAB-ZNFs expression.

To confirm that the observed positive regulation of multiple KRAB-ZNFs by KAP1 was due to changes in KRAB-ZNFs protein stability, HMLE cells were treated with the protein synthesis inhibitor cyclohexemide (CHX) and KRAB-ZNFs degradation rate was analyzed. Levels of multiple KRAB-ZNFs decreased ~35% in control cells and ~60% in KAP1-depleted cells 4 hours following CHX addition. The levels of endogenous ZNF192 protein decreased in a similar fashion (FIGS. 5C and D), indicating that KRAB-ZNFs degrade faster in the absence of KAP1. The level of KAP1 and control GAPDH did not change significantly. In sum, these results indicate that KRAB-ZNF proteins undergo rapid proteasome-dependent turnover characteristic to transcription factors and that direct binding of KAP1 to KRAB-ZNFs protects from proteosomal degradation.

KAP1 Promotes Cell Proliferation, Tumor Growth and Metastasis

To investigate if elevated KAP1 level in tumors is functionally linked to the malignant characteristics of cancer cells, the effect of KAP1 knockdown was analyzed. KAP1 depletion led to a decrease in cell proliferation in all cell lines examined. Strong growth inhibition was also observed in Kap1 knockout MEFs (FIG. 6A). Conversely, overexpression of exogenous wild type KAP1, but not the functionally impaired KAP1 M2 mutant stimulated cell growth (FIG. 6B), indicating that increased KAP1 levels and its repression activity promote cell proliferation.

To assess the role of KAP1 in tumorigenicity in vivo, MDA-MB-231LN cells were used in orthotopic xenograft mouse model. Injection of cells expressing control shRNA into the mammary fat pad of NSG mice resulted in rapid tumor growth as reported previously (33). Inhibition of KAP1 expression using shRNA reduced tumor growth significantly (FIGS. 7A and 21). Conversely, overexpression of exogenous KAP1 resulted in a stimulatory effect on tumor growth (FIG. 7B). These results indicate that KAP1 is a critical component promoting growth of tumor cells in vivo.

The number of lung metastases was scored in tumor bearing mice. KAP1 knockdown tumors produced fewer metastatic colonies and KAP1 overexpressing tumors produced more metastatic colonies than controls (FIG. 7C-D). Since metastasis in these experiments simply correlated with tumor growth, an independent experiment to determine if KAP1 affects lung colonization following tail vein injection was performed. There was a significant decrease in lung bioluminescence in mice xenografted with KAP1 knockdown cells compared to control cells (FIG. 7E-F). These findings demonstrate that KAP1 depletion also inhibits metastatic outgrowth in lungs.

KAP1 Regulates Expression of Genes Promoting Tumor Growth and Metastasis

To investigate the mechanisms by which KAP1 potentially promotes tumor growth and metastasis, we analyzed our microarray data from KAP1-depleted MDA-MB-231LN cells. The genes for PTGS2/COX2, EREG/epiregulin, MMP1 and MMP2 have been previously identified in the lung metastasis gene signature derived from MDA-MB-231LM2 cells as essential factors of aggressive malignant and metastatic behavior (41, 42). Using RT-qPCR we further confirmed their down-regulation in MDA-MB-231LN and HMLE cells following KAP1 knockdown. Conversely, we found up-regulation of some of these genes in cells overexpressing wild type KAP1 (FIG. 7G-H), suggesting that their expression is specifically influenced by KAP1. Changes of COX2 and CD44 expression were confirmed by Western blot (FIG. 7I). Together, these data indicate that KAP1 regulates expression of multiple genes promoting tumor growth and metastasis.

Discussion

Figure 2:
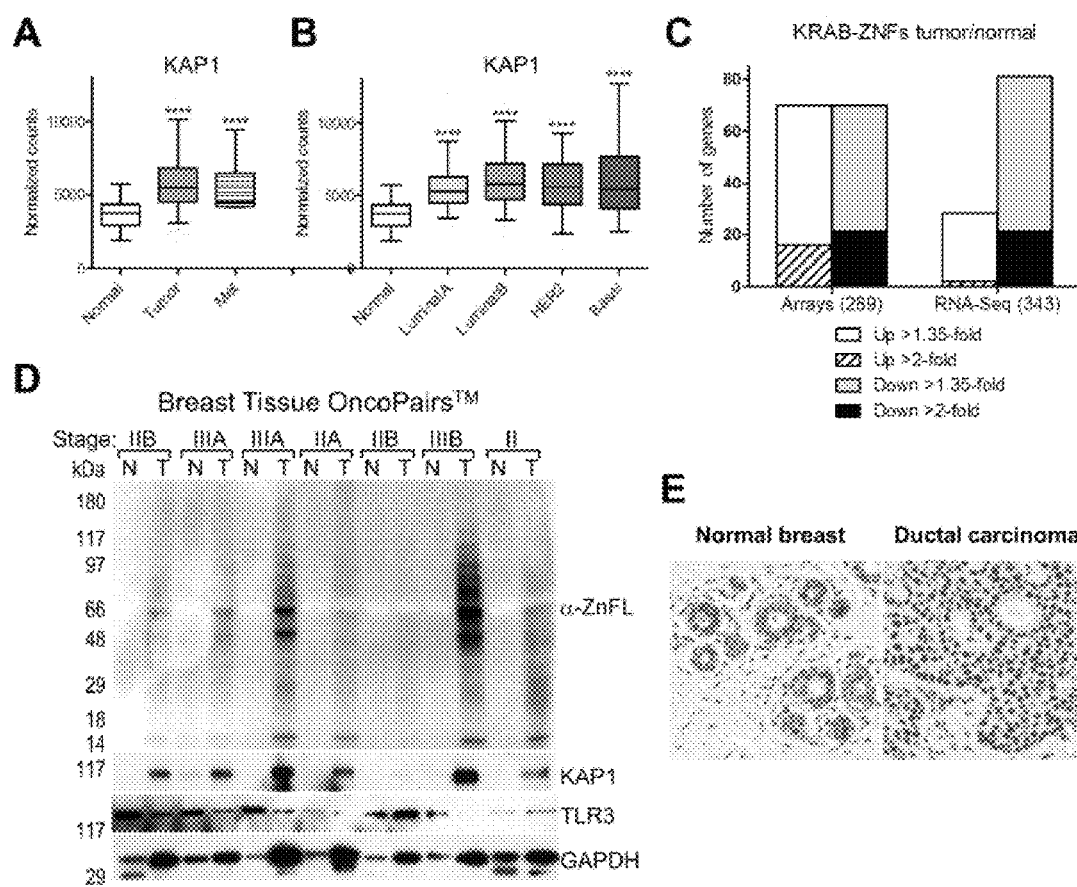
FIG. 2. KAP1 and KRAB-ZNFs are overexpressed in breast tumors. A & B, Analysis of KAP1 in TCGA Breast RNA-Seq data from 105 normal and 798 tumor samples of different subtypes and metastases. Data shown as mean and 5-95% percentile. ****-$P<0.0001$, two-tailed t test. C, Analysis of KRAB-ZNFs expression in TCGA Breast Array (n=527) and RNA-Seq (n=896) datasets, $P<0.05$. D, WB analysis of KAP1 and KRAB-ZNFs in biopsy samples of matched normal (N)-tumor (T) pairs. TLR3 and GAPDH are shown for comparison. E, Representative immunohistochemistry for KAP1 in normal breast and in invasive ductal carcinoma. Images from Human Protein Atlas.
Figure 3:
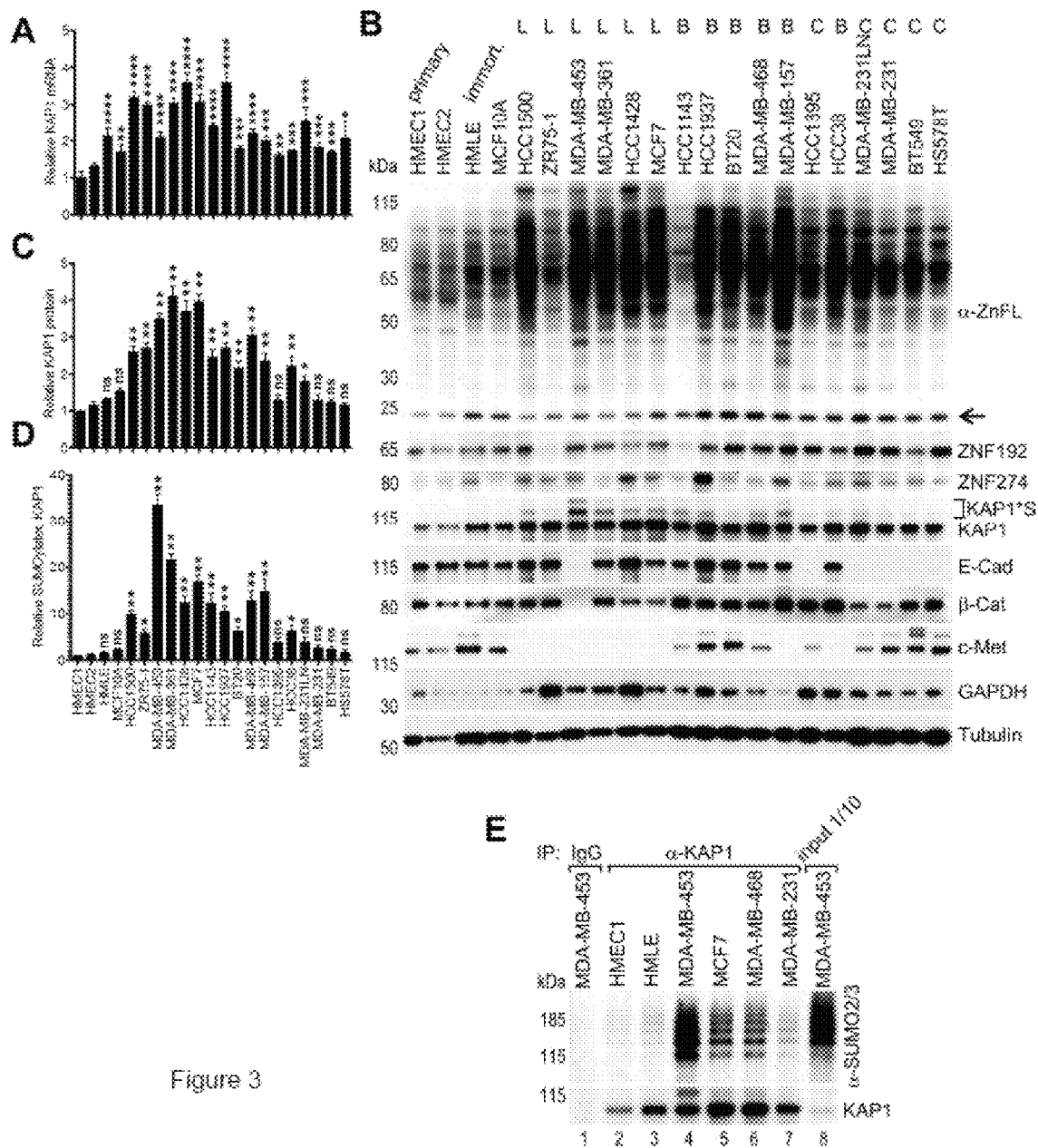
FIG. 3. KAP1 mRNA, protein and SUMOylation are up-regulated in breast cancer cell lines. The indicated cell lines representing luminal (L), basal (B) and claudin-low (C) breast cancer subtypes were analyzed for (A) KAP1 mRNA by RT-qPCR, (B and C) KAP1 protein and (B and D) KAP1 SUMOylation by WB. Arrow points to a ~20 kDa protein band, which serves as loading control. E-cadherin is shown as a reference for luminal and basal cells and as additional loading control. Expression of β-catenin and c-Met oncoproteins as well as GAPDH and tubulin is elevated in cancer cells. KAP1*S—SUMOylated forms of KAP1. Graphs in C and D show densitometric quantification of (B) normalized by tubulin. In A, C, and D, levels for HMEC1 cells were assigned the relative value of 1. E, Immunoprecipitation with control IgG and KAP1 antibody and WB for SUMO2/3 and KAP1. Data shown as mean±SD. *-$P<0.05$, -$P<0.01$, *-$P<0.001$, ****-$P<0.0001$, two-tailed t test.

Elevated expression of KAP1 mRNA has been reported in lung and gastric cancers (25, 43). Herein, we demonstrate that KAP1 is overexpressed in the majority of breast tumors and breast cancer cell lines, at both the mRNA and protein levels (FIGS. 2 and 3, and 12 and 13). KAP1 up-regulation is common for all four intrinsic breast cancer subtypes (FIG. 2B). Interestingly, though KAP1 mRNA is consistently but modestly overexpressed in cancer cells, KAP1 protein is up-regulated at significantly higher levels (FIGS. 2D, 2E, and 15), suggesting that post-transcriptional mechanism(s) could also be at play. In this regard, KAP1 SUMOylation, which is a major indicator of KAP1 repression activity (16, 17), is dramatically increased in cancer cells (FIGS. 3 and 16) and may potentially account for higher KAP1 protein levels. In general, we observed a direct correlation between KAP1 protein and its SUMOylation levels (FIGS. 3C, and 3D; and 11). SUMOylation can compete for the same lysine residues with ubiquitynation and thus may inhibit ubiquitin-dependent protein degradation and increase protein expression levels (44).

Figure 1:
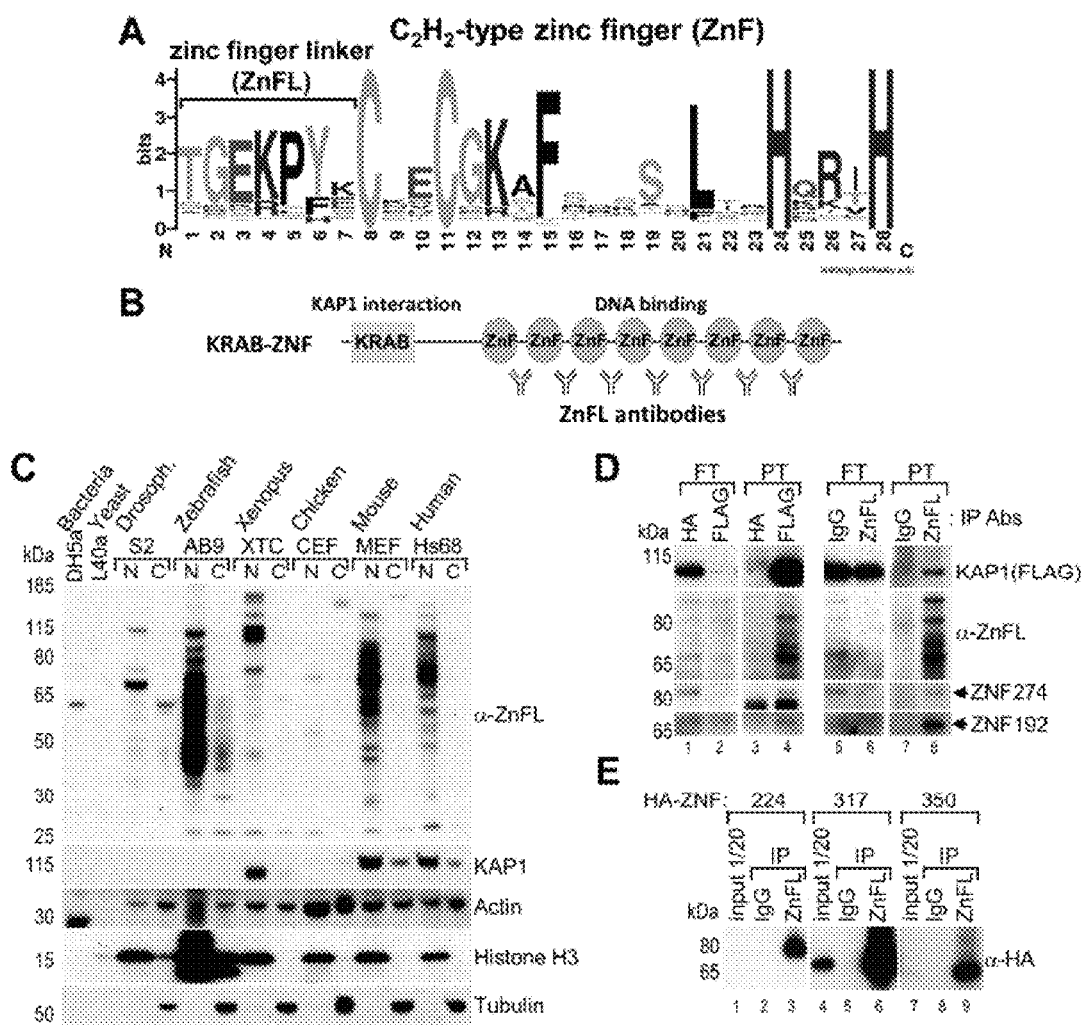
FIG. 1. Characterization of ZnFL antibody. A, Logo representation of amino acid conservation in zinc fingers of human $C_2H_2$-type ZNFs. A high bit score reflects invariant residues C, C, H and H. 7-aa zinc finger linker sequence TGEKPY[K/E] (SEQ ID NO: 2/SEQ ID NO: 3) is highly conserved. B, Domain structure of a typical KRAB-ZNF protein. ZnF—individual zinc finger. ZnFL antibody binds between ZnFs. C, Western blot (WB) analysis with ZnFL and the specified antibodies. The indicated cells were fractionalized into nuclear (N) and cytoplasmic (C) fractions. Histone H3 and tubulin are markers for nuclear and cytoplasmic fractions, respectively. Actin and sc-10809—loading controls. D, KAP1 and KRAB-ZNFs co-immunoprecipitated. HMLE cells expressing FLAG-KAP1 were immunoprecipitated with control HA or FLAG antibody and control rabbit IgG or ZnFL antibody. FT—flow through, PT—pellet. E, IP-WB analysis of transfected HA-KRAB-ZNFs: ZNF224, ZNF317 and ZNF350.

KRAB-ZNF genes constitute one fifth of all human transcription factors (1, 3). Lack of reagents for detection of endogenous levels of KRAB-ZNF proteins has significantly impeded elucidation of their functions. We have developed and characterized a potent ZnFL antibody directed to a highly conserved TGEKPY zinc finger linker and demonstrated that this antibody is capable of detecting multiple ZNF proteins. A similar approach was recently used to develop an antibody to a phosphorylated form of the TGEKPY motif (45). We confirmed the sensitivity and specificity of the ZnFL antibody using multiple approaches (FIG. 1, Table 1).

TABLE 1

Mass spectrometry identification of ZNFs immunoprecipitated by control IgG and ZnFL antibody. SpC-spectral counts.

| Accession Number | SpC IgG | SpC ZnFL | KRAB domain | SCAN domain | Number of ZFs |
|---|---|---|---|---|---|
| Q15072\|OZF/ZNF146 | 0 | 17 | | | 10 |
| Q5VV52\|ZNF691 | 0 | 16 | | | 7 |
| Q9H5H4\|ZNF768 | 0 | 12 | | | 10 |
| Q7L3S4\|ZNF771 | 0 | 10 | | | 8 |
| Q96N38\|ZNF714 | 0 | 9 | + | | 14 |
| Q86W11\|ZSCAN30 | 0 | 8 | | + | 7 |
| Q15776\|ZNF192/ZKSCAN8 | 0 | 8 | + | + | 9 |

TABLE 1-continued

Mass spectrometry identification of ZNFs immunoprecipitated by control IgG and ZnFL antibody. SpC-spectral counts.

| Accession Number | SpC IgG | SpC ZnFL | KRAB domain | SCAN domain | Number of ZFs |
|---|---|---|---|---|---|
| Q3ZCT1\|ZNF260 | 0 | 8 | | | 13 |
| Q96CX3\|ZNF501 | 0 | 8 | | | 9 |
| P17026\|ZNF22 | 0 | 7 | | | 5 |
| P17028\|ZNF24 | 0 | 7 | | + | 4 |
| Q9Y2G7\|ZFP30 | 0 | 4 | + | | 13 |
| Q86UQ0\|ZNF589 | 0 | 4 | + | | 4 |
| Q969J2\|ZKSCAN4 | 0 | 4 | + | + | 7 |
| P17029\|ZKSCAN1 | 0 | 3 | + | + | 6 |
| Q9BRR0\|ZKSCAN3 | 0 | 3 | + | + | 7 |
| P17041\|ZNF32 | 0 | 2 | | | 7 |
| Q14592\|ZNF460 | 0 | 2 | + | | 11 |
| Q96MX3\|ZNF48 | 0 | 2 | | | 12 |
| P36508\|ZNF76 | 0 | 2 | | | 7 |
| Q6DD87\|ZNF787 | 0 | 2 | | | 7 |
| P25490\|YY1 | 0 | 2 | | | 4 |

Overexpression of certain KRAB-ZNF genes in cancer has been documented (10, 31, 32). Here, we analyzed two large TCGA breast datasets and found that dozens of KRAB-ZNFs were up-regulated, while dozens others were down-regulated in breast tumors. Expression of a much smaller number of KRAB-ZNFs changed markedly (>2-fold) (FIG. 2C). At the same time, multiple KRAB-ZNF proteins detected by the ZnFL antibody were overexpressed dramatically in breast tumors (FIG. 2D), suggesting that they could be up-regulated at the protein level rather than mRNA level.

Figure 4:
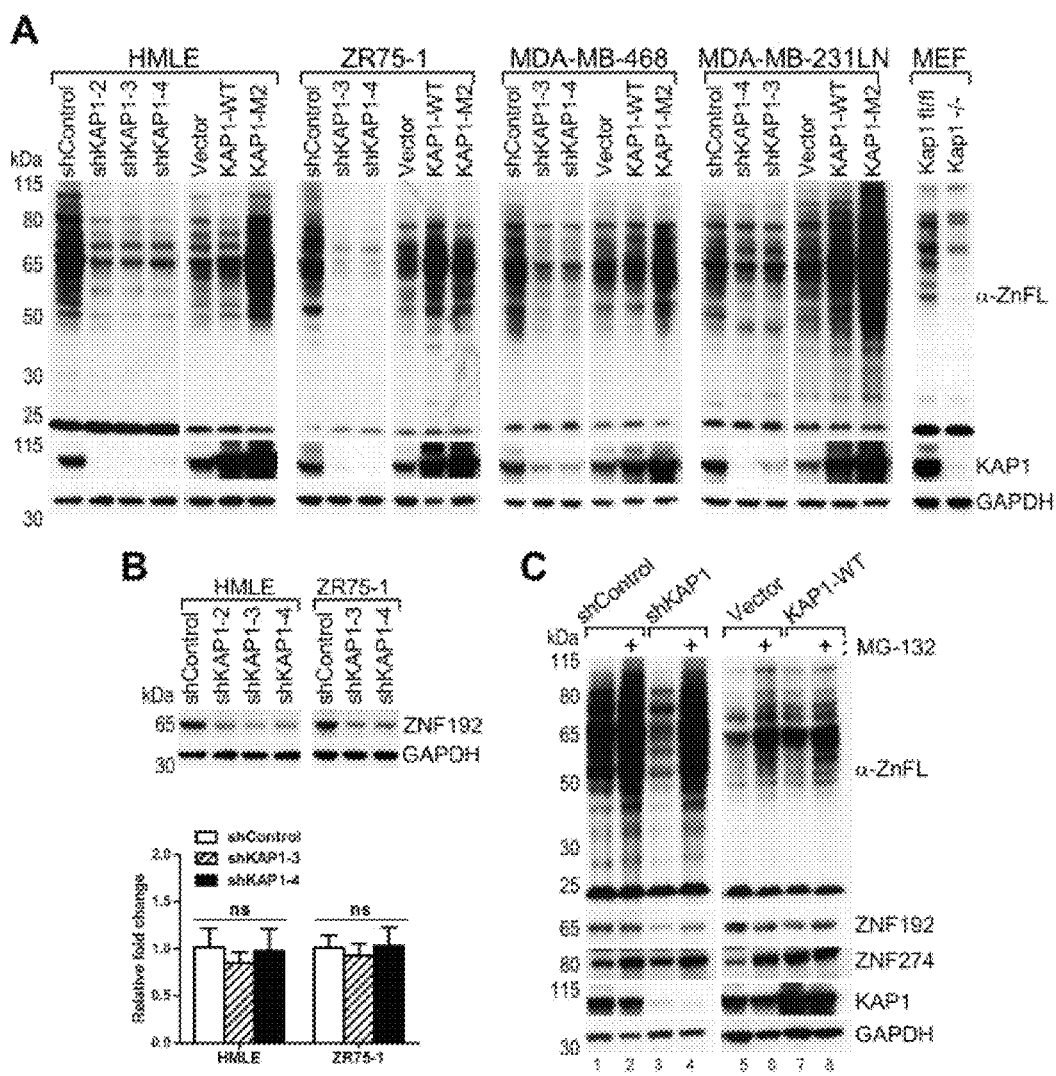
FIG. 4. KAP1 positively regulates expression of multiple KRAB-ZNF proteins. A, WB analysis of KRAB-ZNFs and KAP1 in the indicated cell lines with KAP1 knockdown and overexpression, and in mouse embryonic fibroblasts (MEFs). fl/fl—flox/flox, −/−-KAP1 knockout alleles. B, WB analysis and RT-qPCR of ZNF192 in HMLE and ZR75-1 cells shown in (A). Data shown as mean±SEM. C, WB analysis of the indicated HMLE cell lines treated with vehicle or 10□M MG-132 for 8 hours. GAPDH—loading control.
Figure 5:
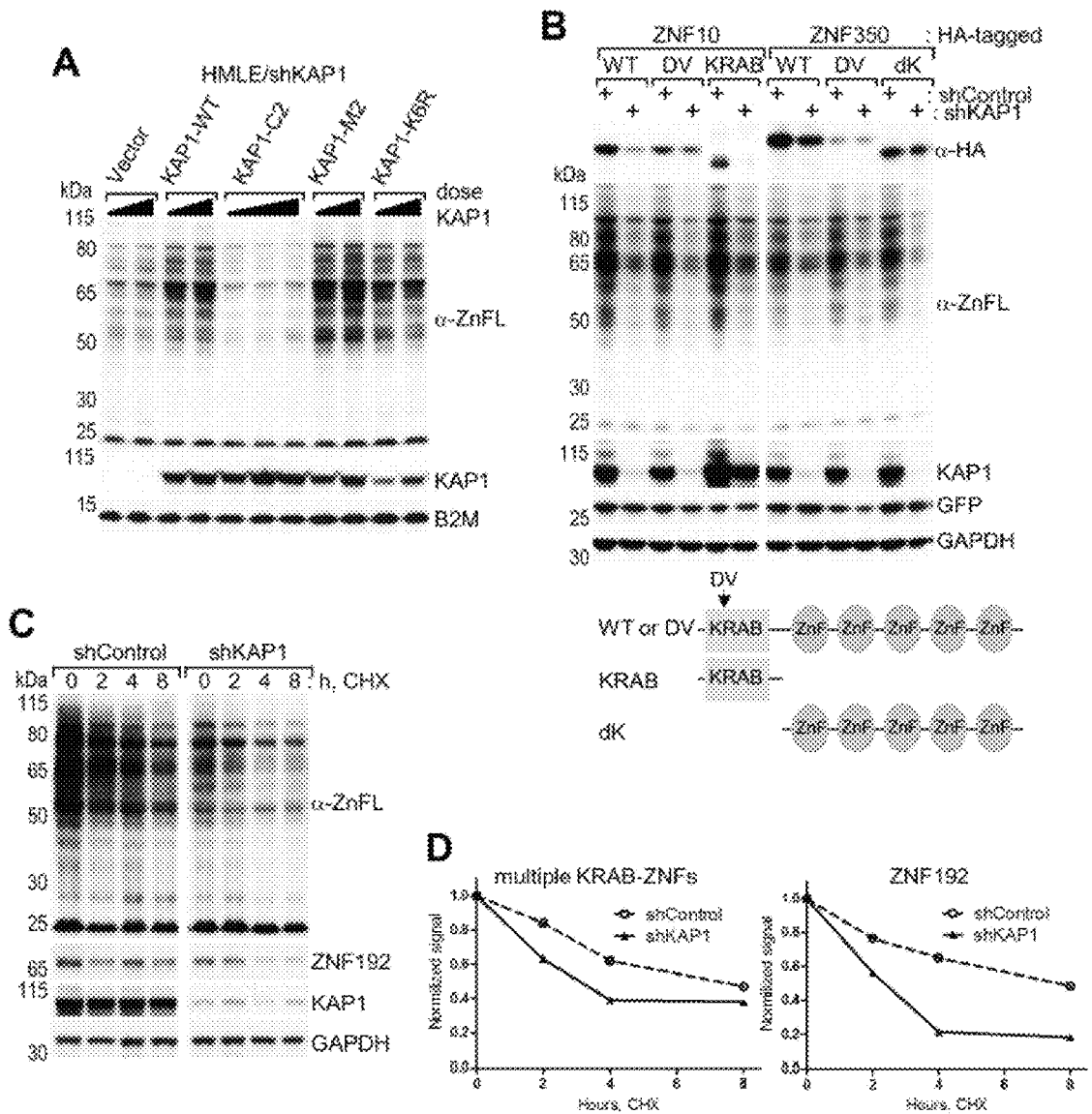
FIG. 5. Expression of KRAB-ZNF proteins depends on their ability to interact with KAP1 and this interaction protects the KRAB-ZNFs from proteasomal degradation. A, WB analysis of KAP1 and KRAB-ZNFs in HMLE/shKAP1 cells reconstituted with vector, wild type and the indicated KAP1 mutants. Increasing doses of KAP1 expressing lentiviruses were used. B2M—loading control. B, WB analysis of H1299 cell lines transfected with HA-tagged ZNF10 and ZNF350. Below is a diagram of the constructs used. WT—wild type, DV—mutant deficient in KAP1 binding, KRAB—KRAB domain only, dK—deleted KRAB domain. GAPDH—loading control. C, WB analysis of HMLE cells treated with 50 μg/ml cycloheximide (CHX) for 0, 2, 4 and 8 hours. D, Quantification of (C) normalized to GAPDH.

Stabilization of individual proteins via assembly into functional multi-protein complexes is a common phenomenon. Stabilization of a sequence-specific transcription factor upon binding to its co-repressor has been documented for E2F-Rb (46), p53-Sin3a (47) and RUNX1-Sin3a (48) interactions. Stabilization is typically achieved via inhibition of ubiquitin-dependent proteasome mediated degradation. Herein, we showed that multiple KRAB-ZNFs undergo rapid proteasome-dependent turnover and are stabilized upon binding to their co-repressor KAP1 (FIGS. 4 and 5). Therefore, significant up-regulation of KRAB-ZNFs observed in breast tumors (FIGS. 2D and E) is likely due to their stabilization by elevated KAP1. Dramatic decrease in the expression of dozens of KRAB-ZNF transcriptional repressors could also explain constitutive chromatin relaxation and reactivation of endogenous retroviral repeats observed in KAP1-deficient cells (21, 49).

Figure 6:
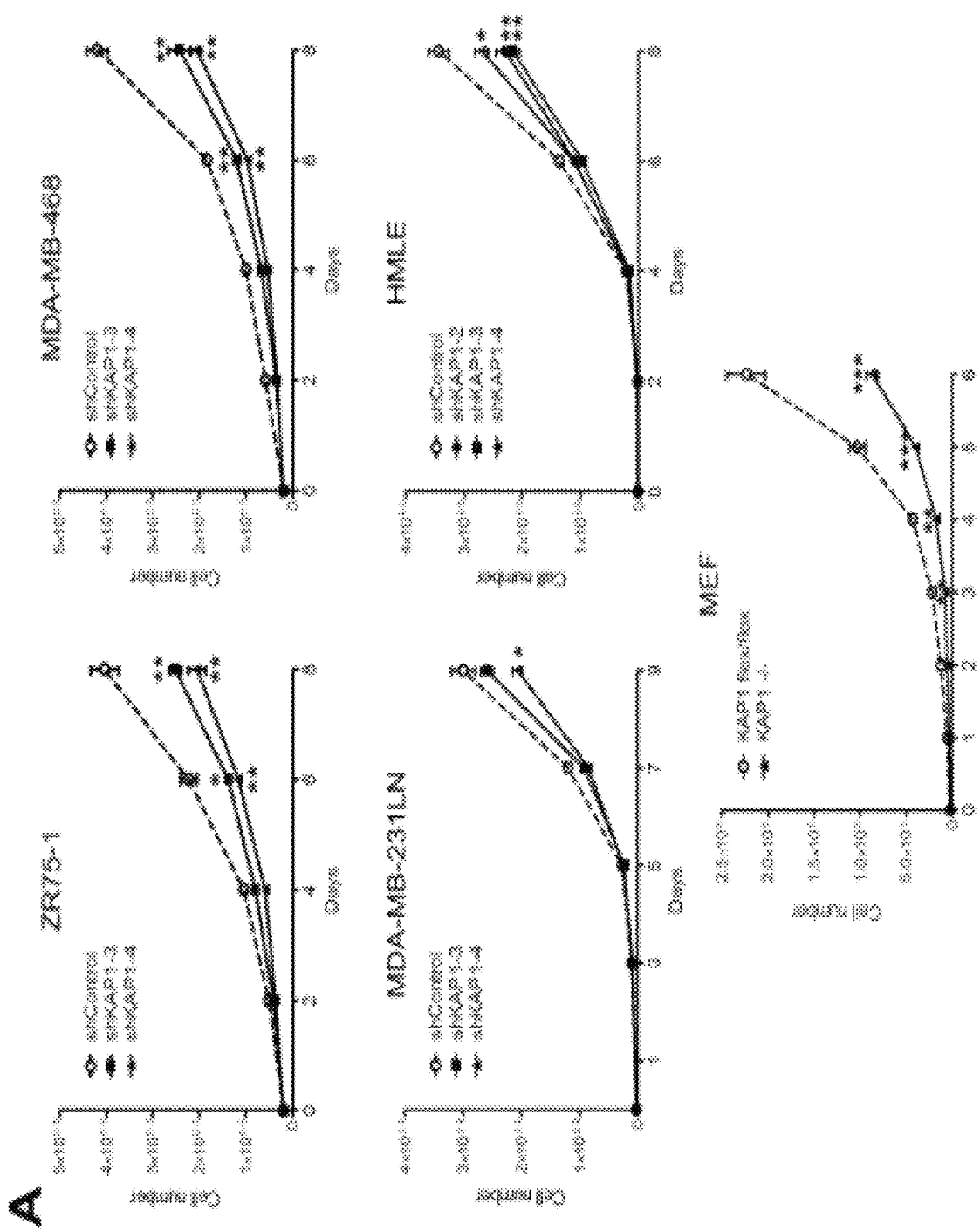
FIG. 6. KAP1 promotes cell proliferation in vitro. A and B, Growth curves for the cell lines characterized in FIG. 4A. Data shown as mean±SEM. *-$P<0.05$, -$P<0.01$ *-$P<0.001$, two-tailed t test.
Figure 6:
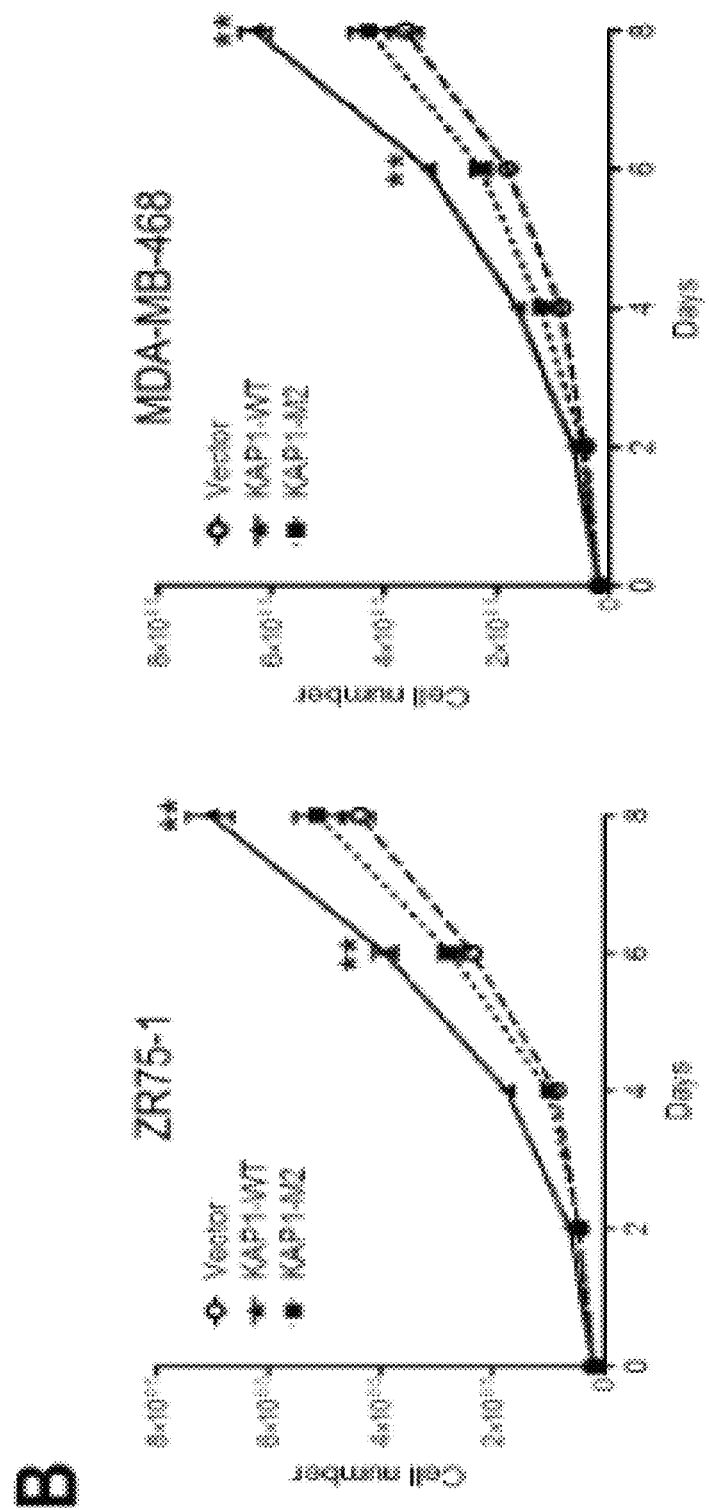
Figure 7:
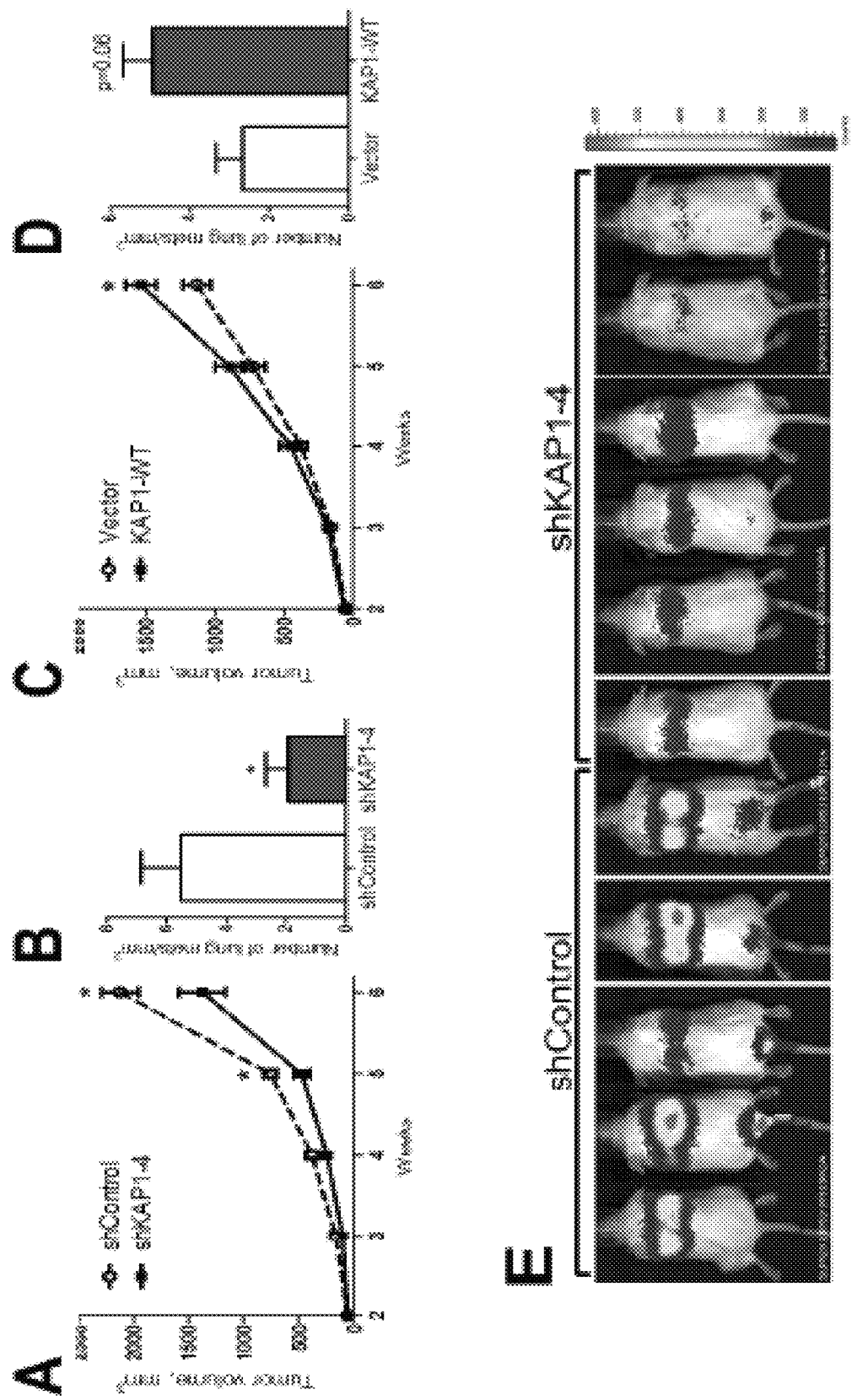
FIG. 7. KAP1 promotes tumor growth and metastasis and regulates expression of cancer-associated genes. A and B, Tumor growth curves of orthotopically injected MDA-MB-231LN cells: shControl (n=4), shKAP1-4 (n=5), vector control (n=4), KAP1-WT (n=5). C and D, Quantification of metastases in lungs of the animals in (A) and (B). E, Bioluminescent images of mice injected intravenously with the indicated MDA-MB-231LN cell lines at 3 weeks post-injection. F, Quantification of (E). G and H, RT-qPCR of genes promoting tumor growth and metastasis in the indicated cell lines. I, WB analysis of COX2 and CD44 in the indicated cell lines. B2M—loading control. Data shown as mean±SEM, *-$P<0.05$, **-$P<0.01$, two-tailed t test.
Figure 7:
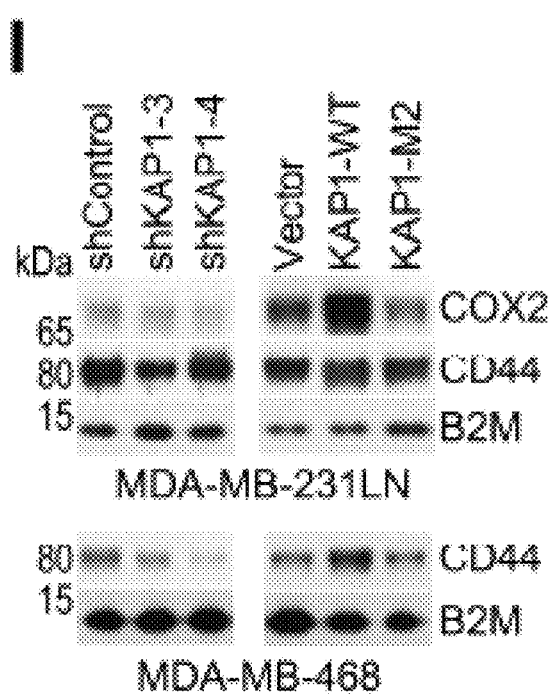
Figure 8:
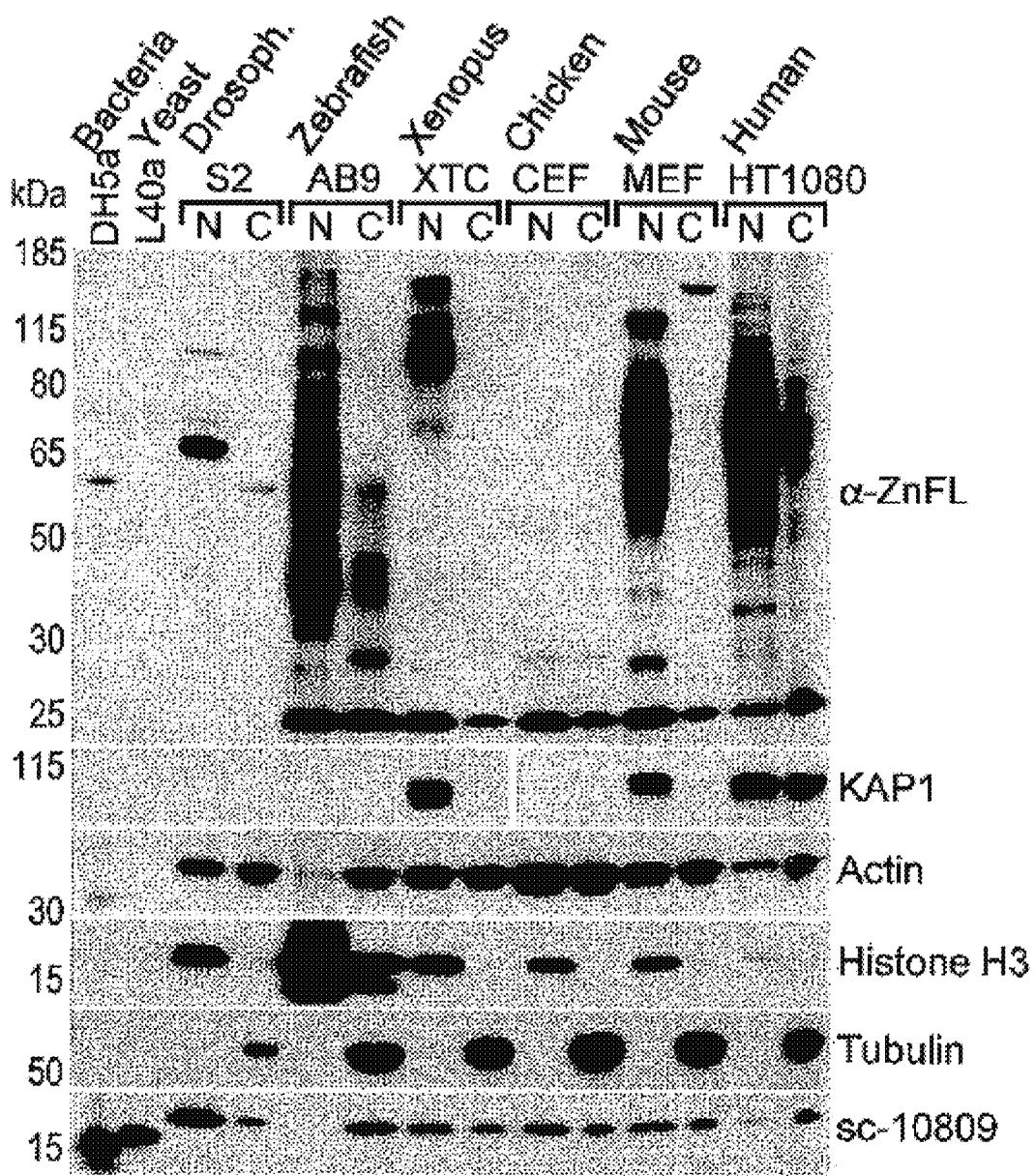
FIG. 8. WB analysis with ZnFL and the specified antibodies.

Previous analyses of the KAP1 role in cancer cell proliferation yielded contradictory results (25, 43). Here, we used multiple shRNAs to knockdown KAP1 in four cell lines and showed that loss of KAP1 inhibited cell proliferation in all cases. Concordantly, overexpression of KAP1 yielded a complementary growth-stimulatory effect (FIG. 6). Consistent with the in vitro studies, inhibition of KAP1 slowed tumor growth and metastasis of MDA-MB-231LN cell xenografts in vivo (FIG. 7).

The mechanism by which KAP1 promotes cell proliferation and tumor growth is unknown but likely involves the action of KAP1 regulated genes. Here, we showed that KAP1 affects expression of many genes implicated in tumor progression and metastasis, particularly PTGS2/COX2, EREG/epiregulin, MMP1 and MMP2 that were previously linked to aggressive tumor behavior (41, 42) (FIG. 7). Identity of individual KRAB-ZNFs involved in regulation of these genes and whether it occurs through direct or indirect mechanism remain to be determined in future studies.

Altogether, we showed that KAP1 is an important positive regulator of cell proliferation and tumor growth. This study suggests that anti-KAP1 drugs should be developed for anticancer therapy. An inhibitor disrupting transcription factor BCL6 with its co-repressor SMRT has been shown to be effective against diffuse large B-cell lymphoma in vivo (50). This opens the possibility that small molecule inhibitors of the KRAB-KAP1 interaction could be developed and potentially be used therapeutically.

Those persons skilled in the art will understand that KAP1 (TRIM28) is a transcriptional regulator in embryonic development that controls stem cell self-renewal, chromatin organization and the DNA damage response, acting as an essential co-repressor for KRAB family zinc finger proteins (KRAB-ZNF). The present invention provides an antibody that recognizes the conserved zinc fingers linker region (ZnFL) in multiple KRAB-ZNF. Here we report that the expression of many KRAB-ZNF along with active SUMO-lyated KAP1 is elevated widely in human breast cancers. KAP1 silencing in breast cancer cells reduced proliferation and inhibited the growth and metastasis of tumor xenografts. Conversely, KAP1 overexpression stimulated cell proliferation and tumor growth. In cells where KAP1 was silenced, we identify multiple downregulated genes linked to tumor progression and metastasis, including EREG/epiregulin, PTGS2/COX2, MMP1, MMP2 and CD44, along with downregulation of multiple KRAB-ZNF proteins. KAP1-dependent stabilization of KRAB-ZNF requires direct interactions with KAP1. The present invention shows that KAP1-mediated stimulation of multiple KRAB-ZNF contributes to the growth and metastasis of breast cancer.

An antibody capable of recognizing the difference between normal cells and cancer cells has been provided in this invention. The antibody of this invention having such as feature is useful as a medicament, a diagnostic drug, and as a research agent. The general knowledge in the art is such that antibodies are structurally well characterized. It is well known that all mammals produce antibodies and that they exist in five isotypes, IgM, IgG, IgD, IgA, and IgE. Antibodies contain an effector portion which is the constant region and a variable region that contains the antigen binding sites in the form of complementarity determining regions and the framework regions. The sequences of constant regions as well as the variable regions subgroups (framework regions) from a variety of species are known and published in the art. It is also well known that antibodies can be made against virtually any protein.

Supplementary Methods

Protein Sequence Alignments

Raw C2H2 zinc finger protein sequence data were downloaded from (1). The Protein Sequence Motif Extractor, Pacific Northwest National Laboratory, Richland, Wash., was used to extract 28 amino acid motifs (canonical zinc finger repeats in the form X7-C-X2-C-X12-H-X3-H) from the sequences of each species. The results were used for generating Logo figures through a web-based tool WebLogo available from University of California, Berkeley.

Microarray Methods

The RMA-normalized intensities of Affymetrix HuEx-1-st-v2 microarrays were used as indicator of gene expression. Statistical and bioinformatics analysis was conducted using the software packages Partek Genomic Suite. Briefly, after vender-recommended quality control and normalization, the control group was used as a baseline to calculate the log 2-transformed intensity ratio before further statistical analysis. The p-values were obtained by an unpaired t-test assuming unequal variance. False discovery rate p-value correction was conducted for multiple hypothesis testing purpose. The microarray data were deposited into the NCBI GEO database as accession number GSE61639.

TCGA Data Analysis

Breast TCGA data were downloaded from the Cancer Genome Atlas (TCGA), National Institutes of Health. Statistical programming software R (version 3.0.1) was used to assemble and process the data. Molecular subtyping was accomplished using the Bioconductor 2.12 Genefu R package.

Mass Spectrometry Analysis

Briefly, MDA-MB-231LN cells were lysed in GLB buffer (non-reducing Laemmli: 50 mM Tris-HCl, pH=6.8, 2% SDS, 10% glycerol). After sonication cell lysate was diluted 1:20 with mIP buffer to bring SDS concentration to 0.1%. Control rabbit IgG or ZnFL antibodies were cross-linked to agarose beads using AminoLink Plus Kit (Pierce). 5 mg of total protein was used for IP with ~200 ug antibody-beads overnight. Immunoprecipitates were washed 5 times with mIP buffer containing 500 mM NaCl. IP'ed proteins were eluted in complete Laemmli buffer, resolved on PAAG and stained with colloidal coomassie. Equivalent gel areas from IgG and ZnFL lanes were cut. Trypsin digestion was performed on the samples using a ProGest robot (DigiLab). Each gel digest was analyzed by nano LC/MS/MS with a Waters NanoAcquity HPLC system interfaced to a Thermo-Fisher Q Exactive. Peptides were loaded on a trapping column and eluted over a 75 µm analytical column at 350 nL/min; both columns were packed with Jupiter Proteo resin (Phenomenex). The injection volume was 30 µL. The mass spectrometer was operated in data-dependent mode, with the Orbitrap operating at 60,000 FWHM and 17,500 FWHM for MS and MS/MS respectively. The fifteen most abundant ions were selected for MS/MS. Data were searched using a local copy of Mascot with the following parameters: Enzyme: Trypsin/P; Database: SwissProt Human (concatenated forward and reverse plus common contaminants); Fixed modification: Carbamidomethyl (C); Variable modifications: Oxidation (M), Acetyl (N-term), Pyro-Glu (N-term Q), Deamidation (N,Q); Mass values: Monoisotopic; Peptide Mass Tolerance: 10 ppm; Fragment Mass Tolerance: 0.02 Da; Max Missed Cleavages: 2. Mascot DAT files were parsed into the Scaffold algorithm for validation, filtering and to create a nonredundant list per sample. Data were filtered using a minimum protein value of 99%, a minimum peptide value of 50% (Prophet scores) and requiring at least two unique peptides per protein. A Supplementary File 1 was developed containing three worksheets: a Protein Report that contains a full list of proteins identified and their molecular weight and spectral counts (SpC); A Protein Report—CON that contains a full list of proteins (with contaminants and reverse hits removed) and their molecular weight and spectral counts (SpC); and a report of Zinc Finger Proteins that contains manually curated list of 22 zinc finger proteins exclusive to the ZnFL sample. Presence of KRAB and SCAN domains and the number of zinc fingers (ZFs) in each protein was determined.

| shRNAs | | | | |
|---|---|---|---|---|
| Gene | Name | Sequence | Company | Clone ID |
| TRIM28/KAP1 | shKAP1-2 | TTCAAGCAATTCAACAAGTTA (SEQ ID NO: 22) | Open Biosystems | V3LHS_640070 |
| | shKAP1-3 | CCGCATGTTCAAGCAATTCAA (SEQ ID NO: 23) | Open Biosystems | V3LHS_640068 |
| | shKAP1-4 | TACAACCTTATTGTTATTGAA (SEQ ID NO: 24) | Open Biosystems | V3LHS_640071 |
| | shControl | TCTCGCTTGGGCGAGAGTAA (SEQ ID NO: 25) | Open Biosystems | RHS4743 |

| SYBR Green based primers | | | |
|---|---|---|---|
| Accession Number | Gene/Primer Name | Sequence | Location |
| NM_006298 | ZNF192 set2-5 | GCCCCAAGAGTCACAAGAG (SEQ ID NO: 26) | Exon 3 (CDS) |
| | ZNF192 set2-3 | CACAGCCATGTCTTCAATCTTC (SEQ ID NO: 27) | Exon 5 (CDS) |
| NM_000963 | PTGS2 set1-5 | ACAGGCTTCCATTGACCAG (SEQ ID NO: 28) | Exon 9 (CDS) |
| | PTGS2 set1-3 | TCACCATAGAGTGCTTCCAAC (SEQ ID NO: 29) | Exon 10 (CDS) |
| NM_001432 | EREG set1-5 | GAATATGTGGCTTTGACCGTG (SEQ ID NO: 30) | Exon 4 (CDS) |
| | EREG set1-3 | TGGATCCCCTGAGGTAACTC (SEQ ID NO: 31) | Exon 5 (CDS) |
| NM_005762 | KAP1-5 | AAGGACCATACTGTGCGCTCTAC (SEQ ID NO: 32) | Exon 3 (CDS) |
| | KAP1-3 | ACGTTGCAATAGACAGTACGTTCAC (SEQ ID NO: 33) | Exon 4 (CDS) |
| NM_012423 | RPL13A set1-5 | TGTTTGACGGCATCCCAC (SEQ ID NO: 34) | Exon 5 (CDS) |
| | RPL13A set1-3 | CTGTCACTGCCTGGTACTTC (SEQ ID NO: 35) | Exon 7 (CDS) |
| NM_021009 | UBC set1-5 | GATTTGGGTCGCAGTTCTTG (SEQ ID NO: 36) | Exon 1 (5'UTR) |
| | UBC set1-3 | CCTTATCTTGGATCTTTGCCTTG (SEQ ID NO: 37) | Exon 2 (CDS) |

-continued

| Accession | Gene/Primer | Sequence | | |
|---|---|---|---|---|
| NM_002592 | PCNA set2-5 | GTCTCTTTGGTGCAGCTCA (SEQ ID NO: 38) | Exon 2 (CDS) | |
| | PCNA set2-3 | ATCTTCGGCCCTTAGTGTAATG (SEQ ID NO: 39) | Exon 3 (CDS) | |
| NM_006009 | TUBA1A set2-5 | TTGTAGACTTGGAACCCACAG (SEQ ID NO: 40) | Exon 2 (CDS) | |
| | TUBA1A set2-3 | ATCTCCTTGCCAATGGTGTAG (SEQ ID NO: 41) | Exon 3 (CDS) | |

PrimeTime based primers

| Accession Number | Gene/Primer Name | Sequence | Company | Assay ID |
|---|---|---|---|---|
| NM_002421 | MMP1 PT for | ACTGAAGGTGTAGCTAGGGTA (SEQ ID NO: 42) | Integrated DNA Technology | Hs.PT.56a.26651575 |
| | MMP1 PT rev | TGAAGATGAAAGGTGGACCAAC (SEQ ID NO: 43) | | |
| | Probe | /56-FAM/AGAATGGGA/ZEN/GAGTCCAAGAGAATGGC/3IABkFQ/ (SEQ ID NO: 44) | | |
| NM_004530 | MMP2 PT for | CCAAGGTCAATGTCAGGAGAG (SEQ ID NO: 45) | Integrated DNA Technology | Hs.PT.56a.38701397 |
| | MMP2 PT rev | GCACCCATTTACACCTACAC (SEQ ID NO: 46) | | |
| | Probe | /56-FAM/ATGACATCA/ZEN/AGGGCATTCAGGAGCT/3IABkFQ/ (SEQ ID NO: 47) | | |

Antibodies

| Protein Name | Company | Catalog number | Reference |
|---|---|---|---|
| KAP1 | Abcam | ab22553 | (2) |
| KAP1 | custom | custom | (16) |
| ZNF192 | Sigma | HPA003483 | |
| ZNF274 | Abnova | H00010782 | (3) |
| SUMO2/3 (8A2) | Abcam | ab81371 | |
| E-cadherin | BD Biosciences | 610181 | |
| β-Catenin (6B3) | Cell Signaling | 9582 | |
| Met | Santa Cruz | sc-161 | |
| COX2 | Cell Signaling | 4842 | |
| CD44 | Santa Cruz | 9960 | |
| GFP | Zymed | 33-2600 | |
| HA | Covance | mms-101p | |
| B2M | Cell Signaling | 9899 | |
| GAPDH | Millipore | MAB374 | |
| Tubulin α | Sigma | T9026 | |
| Actin (I-19) | Santa Cruz | sc-1616 | |
| TLR3 | Imgenex | IMG-315 | |
| histone H3 | Abcam | ab1791 | |
| FLAG beads | Sigma | F2426 | |
| HA beads | Sigma | E6779 | |

Origin of Tissue OncoPair Samples Used in FIG. 2D.

*Novus Biologicals* INSTA-Blot-Breast-Tissue-Onco-Pair-_NBP2-29911.

| Lane | Tissue Type | Grade | Stage | Sex | Age | Diagnosis |
|---|---|---|---|---|---|---|
| 1 | MWM | | | | | |
| 2 | Breast | 1 | IIB | F | 51 | Ductal carcinoma |
| 3 | Breast | | | | | Normal adjacent |
| 4 | Breast | 1 | IIIA | F | 47 | Ductal carcinoma |
| 5 | Breast | | | | | Normal adjacent |
| 6 | Breast | 1 | IIIA | F | 38 | Ductal carcinoma |
| 7 | Breast | | | | | Normal adjacent |
| 8 | Breast | 1 | IIA | F | 60 | Ductal carcinoma |
| 9 | Breast | | | | | Normal adjacent |
| 10 | Breast | 1 | IIB | F | 39 | Ductal carcinoma |
| 11 | Breast | | | | | Normal adjacent |
| 12 | Breast | 2 | IIIB | F | 36 | Ductal carcinoma |
| 13 | Breast | | | | | Normal adjacent |
| 14 | Breast | 2 | II | F | 37 | Ductal carcinoma |
| 15 | Breast | | | | | Normal adjacent |

REFERENCES

1. Vaquerizas J M, Kummerfeld S K, Teichmann S A, Luscombe N M. A census of human transcription factors: Function, expression and evolution. Nat Rev Genet. 2009; 10:252-63.
2. Huntley S, Baggott D M, Hamilton A T, Tran-Gyamfi M, Yang S, Kim J, et al. A comprehensive catalog of human krab-associated zinc finger genes: Insights into the evolutionary history of a large family of transcriptional repressors. Genome Res. 2006; 16:669-77.
3. Corsinotti A, Kapopoulou A, Gubelmann C, Imbeault M, Santoni de Sio F R, Rowe H M, et al. Global and stage specific patterns of kruppel-associated-box zinc finger protein gene expression in murine early embryonic cells. PLoS One. 2013; 8:e56721.
4. Emerson R O, Thomas J H. Adaptive evolution in zinc finger transcription factors. PLoS Genet. 2009; 5:e1000325.
5. Mouse Genome Sequencing C, Waterston R H, Lindblad-Toh K, Birney E, Rogers J, Abril J F, et al. Initial sequencing and comparative analysis of the mouse genome. Nature. 2002; 420:520-62.
6. Frietze S, O'Geen H, Blahnik K R, Jin V X, Farnham P J. Znf274 recruits the histone methyltransferase setdb1 to the 3' ends of znf genes. PLoS One. 2010; 5:e15082.
7. Wolf D, Goff S P. Embryonic stem cells use zfp809 to silence retroviral dnas. Nature. 2009; 458:1201-4.
8. Li X, Ito M, Zhou F, Youngson N, Zuo X, Leder P, et al. A maternal-zygotic effect gene, zfp57, maintains both maternal and paternal imprints. Dev Cell. 2008; 15:547-57.

9. Krebs C J, Khan S, MacDonald J W, Sorenson M, Robins D M. Regulator of sex-limitation krab zinc finger proteins modulate sex-dependent and -independent liver metabolism. Physiol Genomics. 2009; 38:16-28.
10. Urrutia R. Krab-containing zinc-finger repressor proteins. Genome Biol. 2003; 4:231.
11. Margolin J F, Friedman J R, Meyer W K, Vissing H, Thiesen H J, Rauscher F J, 3rd. Kruppel-associated boxes are potent transcriptional repression domains. Proc Natl Acad Sci USA. 1994; 91:4509-13.
12. Peng H, Begg G E, Harper S L, Friedman J R, Speicher D W, Rauscher F J, 3rd. Biochemical analysis of the kruppel-associated box (krab) transcriptional repression domain. J Biol Chem. 2000; 275:18000-10.
13. Iyengar S, Farnham P J. Kap1 protein: An enigmatic master regulator of the genome. J Biol Chem. 286:26267-76.
14. Schultz D C, Ayyanathan K, Negorev D, Maul G G, Rauscher F J, 3rd. Setdb1: A novel kap-1-associated histone h3, lysine 9-specific methyltransferase that contributes to hp1-mediated silencing of euchromatic genes by krab zinc-finger proteins. Genes Dev. 2002; 16:919-32.
15. Quenneville S, Verde G, Corsinotti A, Kapopoulou A, Jakobsson J, Offner S, et al. In embryonic stem cells, zfp57/kap1 recognize a methylated hexanucleotide to affect chromatin and DNA methylation of imprinting control regions. Mol Cell. 2011; 44:361-72.
16. Ivanov A V, Peng H, Yurchenko V, Yap K L, Negorev D G, Schultz D C, et al. Phd domain-mediated e3 ligase activity directs intramolecular sumoylation of an adjacent bromodomain required for gene silencing. Mol Cell. 2007; 28:823-37.
17. Mascle X H, Germain-Desprez D, Huynh P, Estephan P, Aubry M. Sumoylation of the transcriptional intermediary factor 1beta (tif1beta), the co-repressor of the krab multifinger proteins, is required for its transcriptional activity and is modulated by the krab domain. J Biol Chem. 2007; 282:10190-202.
18. Weber P, Cammas F, Gerard C, Metzger D, Chambon P, Losson R, et al. Germ cell expression of the transcriptional co-repressor tif1beta is required for the maintenance of spermatogenesis in the mouse. Development. 2002; 129:2329-37.
19. Messerschmidt D M, de Vries W, Ito M, Solter D, Ferguson-Smith A, Knowles B B. Trim28 is required for epigenetic stability during mouse oocyte to embryo transition. Science. 2012; 335:1499-502.
20. Quenneville S, Turelli P, Bojkowska K, Raclot C, Offner S, Kapopoulou A, et al. The krab-zfp/kap1 system contributes to the early embryonic establishment of site-specific DNA methylation patterns maintained during development. Cell Rep. 2012; 2:766-73.
21. Rowe H M, Jakobsson J, Mesnard D, Rougemont J, Reynard S, Aktas T, et al. Kap1 controls endogenous retroviruses in embryonic stem cells. Nature. 2010; 463:237-40.
22. Santoni de Sio F R, Barde I, Offner S, Kapopoulou A, Corsinotti A, Bojkowska K, et al. Kap1 regulates gene networks controlling t-cell development and responsiveness. FASEB J. 2012; 26:4561-75.
23. Santoni de Sio F R, Massacand J, Barde I, Offner S, Corsinotti A, Kapopoulou A, et al. Kap1 regulates gene networks controlling mouse b-lymphoid cell differentiation and function. Blood. 2012; 119:4675-85.
24. Ho J, Kong J W, Choong L Y, Loh M C, Toy W, Chong P K, et al. Novel breast cancer metastasis-associated proteins. J Proteome Res. 2009; 8:583-94.
25. Yokoe T, Toiyama Y, Okugawa Y, Tanaka K, Ohi M, Inoue Y, et al. Kap1 is associated with peritoneal carcinomatosis in gastric cancer. Ann Surg Oncol. 2010; 17:821-8.
26. Tian C, Xing G, Xie P, Lu K, Nie J, Wang J, et al. Krab-type zinc-finger protein apak specifically regulates p53-dependent apoptosis. Nat Cell Biol. 2009; 11:580-91.
27. Wang C, Ivanov A, Chen L, Fredericks W J, Seto E, Rauscher F J, 3rd, et al. Mdm2 interaction with nuclear corepressor kap1 contributes to p53 inactivation. Embo J. 2005; 24:3279-90.
28. Skapek S X, Jansen D, Wei T F, McDermott T, Huang W, Olson E N, et al. Cloning and characterization of a novel kruppel-associated box family transcriptional repressor that interacts with the retinoblastoma gene product, rb. J Biol Chem. 2000; 275:7212-23.
29. Zheng L, Pan H, Li S, Flesken-Nikitin A, Chen P L, Boyer T G, et al. Sequence-specific transcriptional corepressor function for brca1 through a novel zinc finger protein, zbrk1. Mol Cell. 2000; 6:757-68.
30. Li Z, Wang D, Na X, Schoen S R, Messing E M, Wu G. The vhl protein recruits a novel krab-a domain protein to repress hif-1alpha transcriptional activity. EMBO J. 2003; 22:1857-67.
31. Leary R J, Lin J C, Cummins J, Boca S, Wood L D, Parsons D W, et al. Integrated analysis of homozygous deletions, focal amplifications, and sequence alterations in breast and colorectal cancers. Proc Natl Acad Sci USA. 2008; 105:16224-9.
32. Rink L, Ochs M F, Zhou Y, von Mehren M, Godwin A K. Znf-mediated resistance to imatinib mesylate in gastrointestinal stromal tumor. PLoS One. 2013; 8:e54477.
33. Ice R J, McLaughlin S L, Livengood R H, Culp M V, Eddy E R, Ivanov A V, et al. Nedd9 depletion destabilizes aurora a kinase and heightens the efficacy of aurora a inhibitors: Implications for treatment of metastatic solid tumors. Cancer Res. 2013; 73:3168-80.
34. Tanaka K, Tsumaki N, Kozak C A, Matsumoto Y, Nakatani F, Iwamoto Y, et al. A kruppel-associated box-zinc finger protein, nt2, represses cell-type-specific promoter activity of the alpha 2(xi) collagen gene. Mol Cell Biol. 2002; 22:4256-67.
35. Briers S, Crawford C, Bickmore W A, Sutherland H G. Krab zinc-finger proteins localise to novel kap1-containing foci that are adjacent to pml nuclear bodies. J Cell Sci. 2009; 122:937-46.
36. Lin S Y, Xia W, Wang J C, Kwong K Y, Spohn B, Wen Y, et al. Beta-catenin, a novel prognostic marker for breast cancer: Its roles in cyclin d1 expression and cancer progression. Proc Natl Acad Sci USA. 2000; 97:4262-6.
37. Lengyel E, Prechtel D, Resau J H, Gauger K, Welk A, Lindemann K, et al. C-met overexpression in node-positive breast cancer identifies patients with poor clinical outcome independent of her2/neu. Int J Cancer. 2005; 113:678-82.
38. Iyengar S, Ivanov A V, Jin V X, Rauscher F J, 3rd, Farnham P J. Functional analysis of kap1 genomic recruitment. Mol Cell Biol. 2011; 31:1833-47.
39. Ryan R F, Schultz D C, Ayyanathan K, Singh P B, Friedman J R, Fredericks W J, et al. Kap-1 corepressor protein interacts and colocalizes with heterochromatic and euchromatic hp1 proteins: A potential role for kruppel-associated box-zinc finger proteins in heterochromatin-mediated gene silencing. Mol Cell Biol. 1999; 19:4366-78.
40. Peng H, Begg G E, Schultz D C, Friedman J R, Jensen D E, Speicher D W, et al. Reconstitution of the krab-kap-1 repressor complex: A model system for defining the molecular anatomy of ring-b box-coiled-coil domain-mediated protein-protein interactions. J Mol Biol. 2000; 295:1139-62.
41. Minn A J, Gupta G P, Siegel P M, Bos P D, Shu W, Giri D D, et al. Genes that mediate breast cancer metastasis to lung. Nature. 2005; 436:518-24.
42. Gupta G P, Nguyen D X, Chiang A C, Bos P D, Kim J Y, Nadal C, et al. Mediators of vascular remodelling co-opted for sequential steps in lung metastasis. Nature. 2007; 446:765-70.
43. Chen L, Chen D T, Kurtyka C, Rawal B, Fulp W J, Haura E B, et al. Tripartite motif containing 28 (trim28) can regulate cell proliferation by bridging hdac1/e2f interactions. J Biol Chem. 2012; 287:40106-18.
44. Denuc A, Marfany G. Sumo and ubiquitin paths converge. Biochem Soc Trans. 2010; 38:34-9.
45. Rizkallah R, Alexander K E, Hurt M M. Global mitotic phosphorylation of c2h2 zinc finger protein linker peptides. Cell Cycle. 2011; 10:3327-36.
46. Hofmann F, Martelli F, Livingston D M, Wang Z. The retinoblastoma gene product protects e2f-1 from degradation by the ubiquitin-proteasome pathway. Genes Dev. 1996; 10:2949-59.
47. Zilfou J T, Hoffman W H, Sank M, George D L, Murphy M. The corepressor msin3a interacts with the proline-rich domain of p53 and protects p53 from proteasome-mediated degradation. Mol Cell Biol. 2001; 21:3974-85.
48. Imai Y, Kurokawa M, Yamaguchi Y, Izutsu K, Nitta E, Mitani K, et al. The corepressor msin3a regulates phosphorylation-induced activation, intranuclear location, and stability of aml1. Mol Cell Biol. 2004; 24:1033-43.
49. Ziv Y, Bielopolski D, Galanty Y, Lukas C, Taya Y, Schultz D C, et al. Chromatin relaxation in response to DNA double-strand breaks is modulated by a novel atm- and kap-1 dependent pathway. Nat Cell Biol. 2006; 8:870-6.
50. Cerchietti L C, Ghetu A F, Zhu X, Da Silva G F, Zhong S, Matthews M, et al. A small-molecule inhibitor of bcl6 kills dlbcl cells in vitro and in vivo. Cancer Cell. 2010; 17:400-11.
51. Liu J, Perumal N B, Oldfleld C J, Su E W, Uversky V N, Dunker A K. Intrinsic disorder in transcription factors. Biochemistry. 2006; 45:6873-88.

Supplementary Materials Section References:
1. Emerson R O, Thomas J H. Adaptive evolution in zinc finger transcription factors. PLoS genetics 2009; 5(1): e1000325.
2. O'Geen H, Squazzo S L, Iyengar S, Blahnik K, Rinn J L, Chang H Y, et al. Genome-wide analysis of KAP1 binding suggests autoregulation of KRAB-ZNFs. PLoS genetics 2007; 3(6):e89.
3. Frietze S, O'Geen H, Blahnik K R, Jin V X, Farnham P J. ZNF274 recruits the histone methyltransferase SETDB1 to the 3' ends of ZNF genes. PLoS one 2010; 5(12):e15082.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

It is further to be understood that all values are approximate, and are provided for description.

All patents, applications, publications, test methods, literature, and other materials cited herein are incorporated by reference. If there is a discrepancy between (a) the incorporated by reference patents, applications, publications, test methods, literature, and other materials, and (b) the present application, then the present application's specification, figures, and claims control the meaning of any terms and the scope of the inventions set forth herein.

What is claimed is:

1. Purified rabbit polyclonal pan-ZNF antibodies to human multiple endogenous Kruppel-Associated Box zinc finger proteins, wherein said rabbit polyclonal pan-ZNF antibodies recognize a conserved zinc finger linker sequence comprising the sequence TGEKPY (SEQ ID NO:1), wherein said rabbit polyclonal pan-ZNF antibodies are produced by immunizing a rabbit with a mixture of immunogens Z1 and Z2 peptides, wherein said immunogens Z1 and Z2 peptides comprise the sequences of TGEKPYK (SEQ ID NO:2) and TGEKPYE (SEQ ID NO: 3), and wherein said rabbit polyclonal pan ZNF antibodies detect a zinc finger linker (ZnFL) in cancerous cells.

2. The purified antibodies of claim 1, wherein said conserved zinc finger linker sequence connects two adjacent zinc fingers of a protein.

3. The purified antibodies of claim 1 capable of binding to a zinc finger linker conserved sequence of TGEKPY (SEQ ID NO:1).

4. Purified rabbit polyclonal pan-ZNF antibodies to human multiple endogenous Kruppel-Associated Box zinc finger proteins, wherein said rabbit polyclonal pan-ZNF antibodies recognize a conserved zinc finger linker sequence wherein said sequence is one selected from the group consisting of TGEKPY SEQ ID NO:1), HQRIHTGEKPYK SEQ ID NO:4), HQRIHTGEKPYE (SEQ ID NO:5), HKRIHTGEKPYK (SEQ ID NO:6), HKRIHTGEKPYE (SEQ ID NO: 7), HERIHTGEKPYK (SEQ ID NO:8), and HERIHTGEKPYE (SEQ ID NO:9), wherein said rabbit polyclonal pan-ZNF antibodies are produced by immunizing a rabbit with a mixture of immunogens Z1 and Z2 peptides, wherein said immunogens Z1 and Z2 peptides comprise the sequences of TGEKPYK (SEQ ID NO:2) and TGEKPYE (SEQ ID NO: 3), and wherein said rabbit polyclonal pan ZNF antibodies detect a zinc finger linker (ZnFL) in cancerous cells.

5. The purified antibodies of claim 1 wherein said cancerous cells are cells selected from the group consisting of breast, lung, liver, gastric, and prostate tumors.

6. A diagnostic kit consisting essentially of purified rabbit polyclonal pan-ZNF antibodies to human multiple endogenous Kruppel-Associated Box zinc finger proteins, wherein said rabbit polyclonal pan-ZNF antibodies recognize a conserved zinc finger linker sequence comprising the sequence TGEKPY (SEQ ID NO:1), wherein said rabbit polyclonal pan-ZNF antibodies are produced by immunizing a rabbit with a mixture of immunogens Z1 and Z2 peptides, wherein said immunogens Z1 and Z2 peptides comprise the sequences of TGEKPYK (SEQ ID NO:2) and TGEKPYE (SEQ ID NO: 3), and wherein said rabbit polyclonal pan-ZNF antibodies detect a zinc finger linker (ZnFL) in cancerous cells.

7. The diagnostic kit of claim 6 wherein said conserved zinc finger linker sequence connects two adjacent zinc fingers of a protein.

8. A diagnostic kit consisting essentially of purified rabbit polyclonal pan-ZNF antibodies to human multiple endogenous Kruppel-Associated Box zinc finger proteins, wherein said rabbit polyclonal pan-ZNF antibodies recognize a conserved zinc finger linker sequence wherein said sequence is one selected from the group consisting of HQRIHTGEKPYK (SEQ ID NO:4), HQRIHTGEKPYE (SEQ ID NO:5), HKRIHTGEKPYK (SEQ ID NO:6), HKRIHTGEKPYE (SEQ ID NO:7), HERIHTGEKPYK (SEQ ID NO:8), and HERIHTGEKPYE (SEQ ID NO:9), wherein said rabbit polyclonal pan-ZNF antibodies are produced by immunizing a rabbit with a mixture of immunogens Z1 and Z2 peptides, wherein said immunogens Z1 and Z2 peptides comprise the sequences of TGEKPYK (SEQ ID NO:2) and TGEKPYE (SEQ ID NO: 3), and wherein said rabbit polyclonal pan-ZNF antibodies detect a zinc finger linker (ZnFL) in cancerous cells.

9. The diagnostic kit of claim 8 wherein said cancerous cells being detected is a cell selected from the group of a breast cancer cell, a liver cancer cell, a lung cancer cell, a gastric cancer cell, and a prostate cancer cell.

10. A pharmaceutical composition comprising a therapeutically effective amount of purified rabbit polyclonal pan-ZNF antibodies to human multiple endogenous Kruppel-Associated Box zinc finger proteins, wherein said rabbit polyclonal pan-ZNF antibodies recognize a conserved zinc finger linker sequence comprising the sequence TGEKPY (SEQ ID NO:1), wherein said rabbit polyclonal pan-ZNF antibodies are produced by immunizing a rabbit with a mixture of immunogens Z1 and Z2 peptides, wherein said immunogens Z1 and Z2 peptides comprise the sequences of TGEKPYK (SEQ ID NO:2) and TGEKPYE (SEQ ID NO: 3), and wherein said rabbit polyclonal pan ZNF antibodies detect a zinc finger linker (ZnFL) in cancerous cells.

11. A pharmaceutical composition comprising a therapeutically effective amount of rabbit polyclonal pan-ZNF antibodies to human multiple endogenous Kruppel-Associated Box zinc finger proteins, wherein said rabbit polyclonal pan-ZNF antibodies recognize a conserved zinc finger linker sequence wherein said sequence is one selected from the group consisting of HQRIHTGEKPYK (SEQ ID NO:4), HQRIHTGEKPYE (SEQ ID NO:5), HKRIHTGEKPYK (SEQ ID NO:6), HKRIHTGEKPYE (SEQ ID NO:7), HERIHTGEKPYK (SEQ ID NO:8), and HERIHTGEKPYE (SEQ ID NO:9), wherein said rabbit polyclonal pan-ZNF antibodies are produced by immunizing a rabbit with a mixture of immunogens Z1 and Z2 peptides, wherein said immunogens Z1 and Z2 peptides comprise the sequences of TGEKPYK (SEQ ID NO:2) and TGEKPYE (SEQ ID NO: 3), and wherein said rabbit polyclonal pan-ZNF antibodies detect a zinc finger linker (ZnFL) in cancer cells.

\* \* \* \* \*